US012589235B2

(12) United States Patent
Spanier

(10) Patent No.: US 12,589,235 B2
(45) Date of Patent: Mar. 31, 2026

(54) FLEXIBLE OUTFLOW CANNULA WITH SHAPED OUTLETS

(71) Applicant: ABIOMED, Inc., Danvers, MA (US)

(72) Inventor: Gerd Spanier, Aachen (DE)

(73) Assignee: ABIOMED, INC., Danvers, MA (US)

( * ) Notice: Subject to any disclaimer, the term of this patent is extended or adjusted under 35 U.S.C. 154(b) by 295 days.

(21) Appl. No.: 18/213,324

(22) Filed: Jun. 23, 2023

(65) Prior Publication Data

US 2023/0414921 A1     Dec. 28, 2023

Related U.S. Application Data

(60) Provisional application No. 63/355,217, filed on Jun. 24, 2022.

(51) Int. Cl.
    *A61M 60/139*       (2021.01)
    *A61M 25/00*       (2006.01)
            (Continued)

(52) U.S. Cl.
    CPC ...... *A61M 60/139* (2021.01); *A61M 25/0054* (2013.01); *A61M 25/007* (2013.01);
            (Continued)

(58) Field of Classification Search
    CPC .............. A61M 60/13; A61M 25/0012; A61M 25/0045; A61M 2025/0024; A61M 2025/0047; A61M 2025/0048; A61M 25/0023; A61M 25/01; A61M 60/216; A61M 60/865; A61M 60/857; A61M 2205/04; A61M 2205/75; A61M 2210/125; A61M 2210/127; A61M 25/0054; A61M 25/007; A61M 60/139; A61M 60/174;
(Continued)

(56) References Cited

U.S. PATENT DOCUMENTS 10,478,538 B2    11/2019   Scheckel et al.
11,020,584 B2    6/2021   Siess et al.
(Continued)

OTHER PUBLICATIONS

International Search Report, and Written Opinion, for corresponding PCT application No. PCT/US2023/026055, dated Sep. 27, 2023.

*Primary Examiner* — Jon Eric C Morales
(74) *Attorney, Agent, or Firm* — Meagher Emanuel Laks Goldberg & Liao, LLP

(57)          ABSTRACT

A blood pump may be provided that may include a pump housing and a catheter operably coupled to the pump housing. The pump may include a flexible outflow cannula having a proximal portion operably coupled to the catheter, blood flow outlets, and a distal portion operably coupled to the pump housing. The proximal portion of the flexible outflow cannula may have a coupled portion coupled to the catheter and an uncoupled portion extending distally from the coupled portion, where at least one slit may be formed through the entire coupled portion. The slit may extend distally from the coupled portion through at least a portion of the uncoupled portion and connect to a proximal end of at least one of the blood flow outlets ("cut outlets"), the cut outlets having a tapered proximal end and extending distally from the uncoupled portion.

19 Claims, 21 Drawing Sheets

(51) Int. Cl.

| | |
|---|---|
| *A61M 60/13* | (2021.01) |
| *A61M 60/174* | (2021.01) |
| *A61M 60/242* | (2021.01) |
| *A61M 60/414* | (2021.01) |
| *A61M 60/416* | (2021.01) |
| *A61M 60/808* | (2021.01) |

(52) U.S. Cl.
CPC .......... *A61M 60/13* (2021.01); *A61M 60/174* (2021.01); *A61M 60/242* (2021.01); *A61M 60/414* (2021.01); *A61M 60/416* (2021.01); *A61M 60/808* (2021.01); *A61M 2205/04* (2013.01); *A61M 2205/75* (2013.01); *A61M 2210/125* (2013.01); *A61M 2210/127* (2013.01)

(58) Field of Classification Search
CPC .............. A61M 60/237; A61M 60/242; A61M 60/414; A61M 60/416; A61M 60/808; A61M 60/81; A61M 60/812; A61M 2025/0188; A61M 2025/0675; A61M 2039/1061; A61M 25/0009; A61M 25/005; A61M 25/0097; A61M 25/0668; A61M 39/02; A61M 60/135; A61M 60/165

See application file for complete search history.

(56) References Cited

U.S. PATENT DOCUMENTS

| | | | |
|---|---|---|---|
| 11,191,944 B2 | 12/2021 | Tuval et al. | |
| 2021/0213273 A1* | 7/2021 | Spanier ............... | A61M 60/857 |
| 2023/0063196 A1* | 3/2023 | Spanier ............... | A61M 60/857 |

* cited by examiner

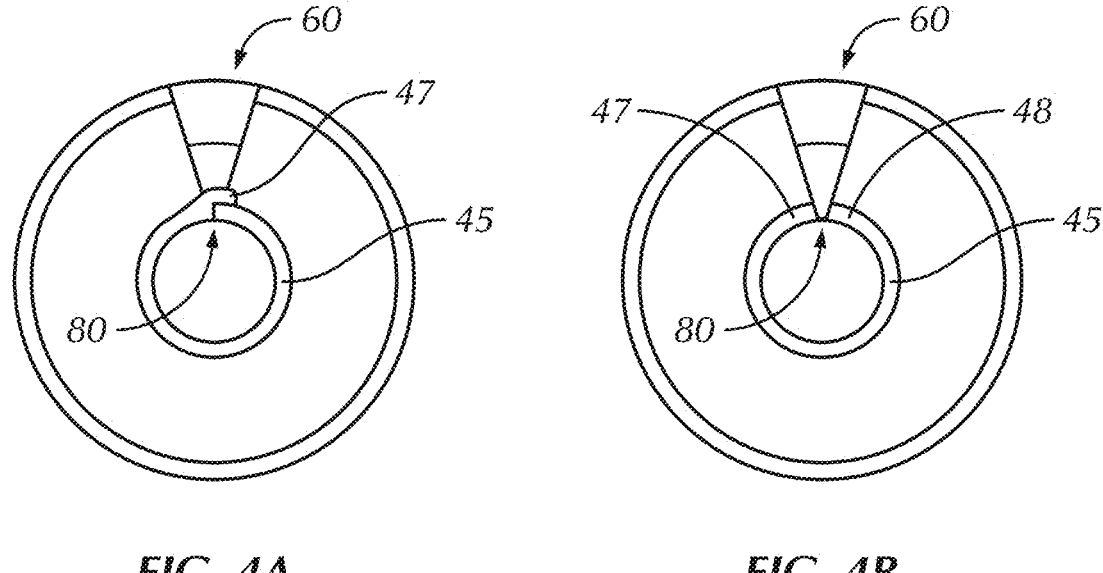
FIG. 4A                    FIG. 4B

FLEXIBLE OUTFLOW CANNULA WITH SHAPED OUTLETS

CROSS-REFERENCE TO RELATED APPLICATIONS

The present application claims priority to U.S. Provisional Patent App. No. 63/355,217, filed Jun. 24, 2022, the contents of which are incorporated by reference herein in its entirety.

TECHNICAL FIELD

The present disclosure is drawn to blood pump outflow cannulas with shaped (such as V-shaped) outlets.

BACKGROUND

Blood pumps, which may use outflow cannula, are used for ensuring blood is moved from one area of a person's body to an adjacent area, around blockages, valves, etc. For example, a blood pump may be used to move blood from a left ventricle to past an aortic valve.

However, as blood pumps decrease in size, two challenges arise: being able to manufacture the increasingly smaller devices, while still ensuring that the device does not facilitate thrombus formation.

BRIEF SUMMARY

In some embodiments, a blood pump may be provided. The blood pump may include a pump housing having a blood flow inlet, a catheter operably coupled to a proximal end of the pump housing, a flexible outflow cannula that may have a proximal portion operably coupled to the catheter, a plurality of blood flow outlets, and a distal portion operably coupled to the pump housing, where the pump housing and flexible outflow cannula may define a blood flow path from the blood flow inlet of the pump housing to the plurality of blood flow outlets, and an impeller that may be arranged within the pump housing and configured to be rotatable about an axis of rotation for conveying blood from the blood flow inlet to the plurality of blood flow outlets.

The catheter may have an outer diameter smaller than an outer diameter of the pump housing. The proximal portion of the flexible outflow cannula may have a coupled portion coupled to the catheter and an uncoupled portion extending distally from the coupled portion. At least one slit may be formed through the entire coupled portion and extending to a proximal end of the flexible outflow cannula. The plurality of blood flow outlets may include at least one cut outlet, and the slit may extend distally from the coupled portion through at least a portion of the uncoupled portion and connect to a proximal end of at least one of the cut outlets. The cut outlets may have a tapered proximal end and extend distally from the uncoupled portion.

In some embodiments, the plurality of blood flow outlets consists of four blood flow outlets, and the four blood flow outlets consist of exactly one cut outlet or exactly two cut outlets. In some embodiments, each of the plurality of blood flow outlets may be spaced equally distant circumferentially from adjacent blood flow outlets. In some embodiments, the cut outlets consist of one blood flow outlet.

In some embodiments, the flexible outflow cannula may include an intermediate portion extending between the distal end portion and the proximal end portion, the intermediate portion having an outer diameter that may be larger than the outer diameter of the pump housing.

In some embodiments, each of the plurality of blood flow outlets may be positioned at least partially in the intermediate portion, and only the cut outlets are positioned at least partially in both the proximal end portion and the intermediate portion.

In some embodiments, the flexible outflow cannula may be defined by a substantially tubular member having a sidewall thickness of less than 20 microns.

In some embodiments, the cut outlets each may include a distal portion, a proximal portion, and an intermediate portion between the distal portion and proximal portion, the intermediate portion having substantially parallel sides. In some embodiments, the proximal portion of the cut outlets forms a cut with straight, non-parallel sides. In some embodiments, the proximal portion of the cut outlets forms a cut with concave sides. In some embodiments, the proximal portion of the cut outlets forms a cut with convex sides. In some embodiments, a proximal end of the proximal portion has a width that may be equal to a width of the slit across the coupled portion. In some embodiments, a proximal end of the proximal portion has a width that may be greater than a width of the slit across the coupled portion.

In some embodiments, the slit may be configured to allow at least a first portion of the coupled portion of the proximal end portion to overlap a second portion of the coupled portion of the proximal end portion. In some embodiments, the slit may be configured to prevent a first portion of the coupled portion of the proximal end portion from overlapping with a second portion of the coupled portion of the proximal end portion.

In some embodiments, the blood pump may include a filter in fluid communication between: (a) an interior volume of a blood vessel in which the blood pump may be inserted, external to the pump housing, and (b) the blood flow inlet, the filter comprising a plurality of generally helical first struts wound about the longitudinal axis and a plurality of second struts, the first and second struts collectively defining a plurality of apertures therebetween.

In some embodiments, the pump housing, the impeller, and any filter may each alternatingly radially compressible and radially expandable.

In some embodiments, the pump housing may be configured, when radially compressed, to longitudinally lengthen an amount that depends on an amount by which the pump housing may be radially compressed, and the filter may be configured, when radially compressed, to longitudinally lengthen an amount that depends on an amount by which the filter may be radially compressed such that, for a given amount of radial compression, the filter and the pump housing longitudinally lengthen about equal amounts.

In some embodiments, the catheter, the pump housing, the impeller, and the filter may be configured for use in a living patient, such that each aperture of the plurality of apertures may be sized to prevent ingestion, by the blood flow inlet, of heart tissue of the living patient.

In some embodiments, each aperture of the plurality of apertures may have a largest dimension less than or equal to about 0.5 mm. In some embodiments, each aperture of the plurality of apertures may have a largest dimension less than or equal to about 0.4 mm. In some embodiments, each aperture of the plurality of apertures may have an area less than or equal to about 0.09 mm$^2$. In some embodiments, each aperture of the plurality of apertures may have an area less than or equal to about 0.16 mm$^2$. In some embodiments, the plurality of apertures may have a size that increases monotonically along the longitudinal axis.

In some embodiments, the generally helical first struts may be wound clockwise about the longitudinal axis, and the second struts are generally helically wound counterclockwise about the longitudinal axis. In some embodiments, the generally helical first struts may be wound in a first direction about the longitudinal axis, and the second struts are generally helically wound in the first direction about the longitudinal axis. In some embodiments, each strut of at least a subset of the second struts may lie in a respective plane that contains the longitudinal axis. In some embodiments, each aperture of at least a subset of the plurality of apertures may have a general rhombus or rhomboid shape. In some embodiments, the generally helical first struts may include a plurality of first filaments, the second struts may include a plurality of second filaments and the first and second filaments may be woven together, such that the plurality of apertures may be defined between respective adjacent first and second woven filaments. In some embodiments, the filter may include a tube having a wall, wherein the plurality of apertures may include a plurality of openings defined through the wall. In some embodiments, the tube may include a generally funnel-shaped tube. In some embodiments, the wall may be about 10-100 μm thick.

In some embodiments, the pump housing may include a plurality of third struts that collectively define a plurality of third apertures therebetween, and at least some of the first and second struts register radially over respective ones of the third struts.

In some embodiments, each strut of at least a subset of the first struts may include a fork that includes a plurality of tines, wherein a plurality of the first struts and a plurality of the second struts may extend between a pair of the tines and collectively may define a plurality of the apertures therebetween. In some embodiments, each first strut that includes a fork may be wider than each first strut that does not include a fork.

In some embodiments, the plurality of apertures may be arranged in a plurality of generally circumferential, relative to the longitudinal axis, rows of equal-sized apertures, where one or more of the rows have different numbers of apertures from others of the rows.

In some embodiments, a first row of the plurality of generally circumferential rows may include more apertures than a second row of the plurality of generally circumferential rows, and each aperture of the first row may have a smaller area than each aperture of the second row.

In some embodiments, the apertures may be arranged in a plurality of generally circumferential, relative to the longitudinal axis, bands of about equal-sized apertures, wherein size of the apertures in each of the plurality of bands increases monotonically along the longitudinal axis.

In some embodiments, the filter may include a distal portion and a proximal portion, the distal portion may monotonically increase in diameter in a proximal direction along the longitudinal axis, the proximal portion may monotonically decrease in diameter in the proximal direction along the longitudinal axis and at least a portion of the plurality of apertures may be disposed on the distal portion.

In some embodiments, the generally helical first struts and the second struts may be absent any circumferential, relative to the longitudinal axis, struts.

BRIEF DESCRIPTION OF DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

FIGS. 4A and 4B are illustrations of end views of flexible outflow cannulas.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION

The following description and drawings merely illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be only for illustrative purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or, unless otherwise indicated (e.g., "or else" or "or in the alternative"). Also, the various embodiments described herein are not necessarily mutually exclusive, as some embodiments can be combined with one or more other embodiments to form new embodiments.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others. Those skilled in the art and informed by the teachings herein will realize that the disclosed may also be applicable to various other technical areas or embodiments.

To provide a small blood pump that, e.g., improves manufacturability and minimizes a risk of forming thrombi, a blood pump with a particular flexible outflow cannula may be provided.

Figure 1:
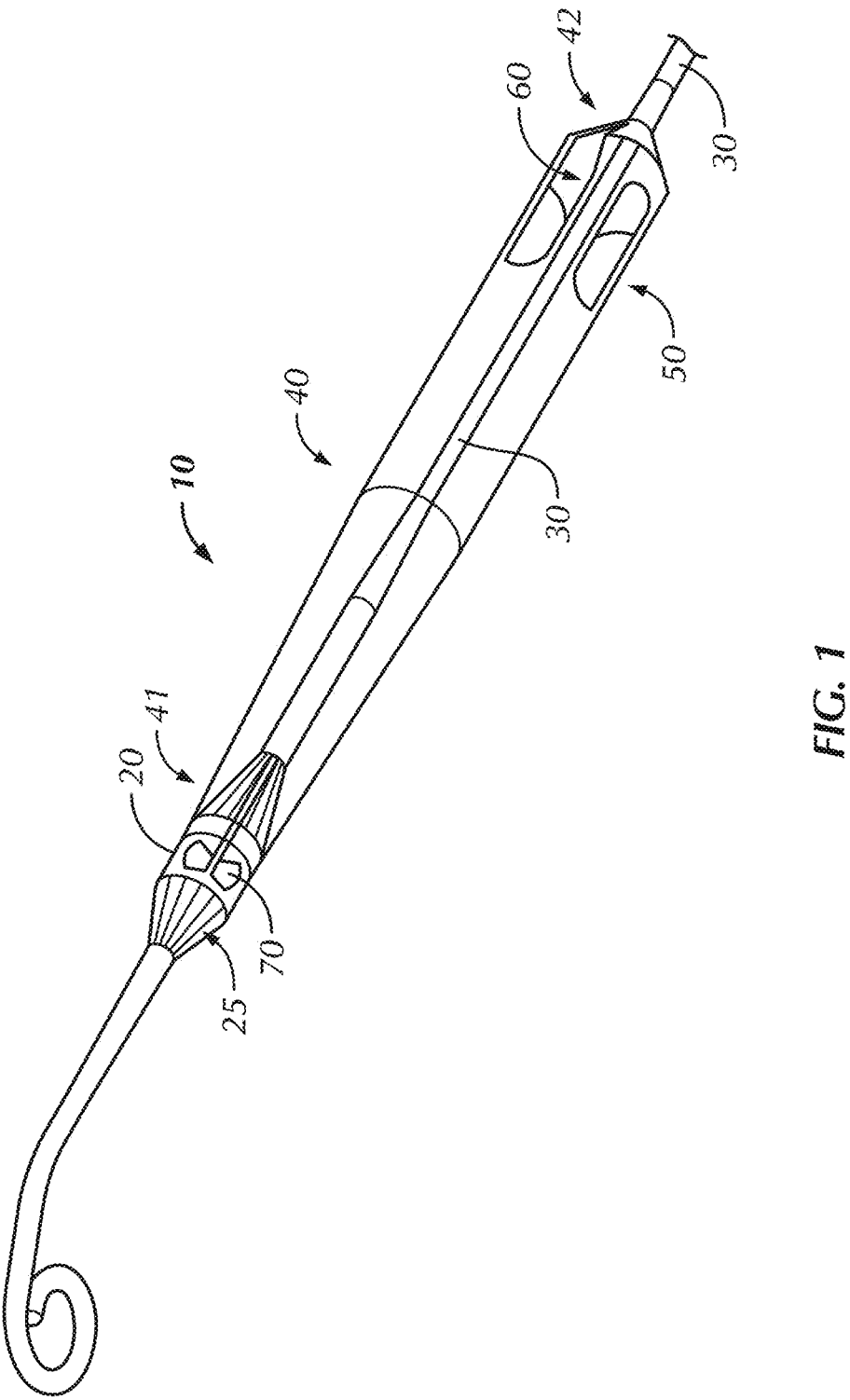
FIG. 1 is an illustration of a perspective view of a blood pump.

Referring to FIG. 1, embodiments of a blood pump 10 may include a pump housing 20. The pump housing may have a blood flow inlet 25. The blood pump may include a catheter 30 operably coupled to a proximal end of the pump housing.

The blood pump may include a flexible outflow cannula 40 that may have a proximal portion 42 operably coupled to the catheter, a plurality of blood flow outlets 50, 60, and a distal portion 41 operably coupled to the pump housing. The pump housing and flexible outflow cannula may define a blood flow path from the blood flow inlet of the pump housing to the plurality of blood flow outlets.

An impeller 70 may be arranged within the pump housing and configured to be rotatable about an axis of rotation for conveying blood from the blood flow inlet to the plurality of blood flow outlets.

Figures 2, 3A, 3B, 3C, 3D, 3E:
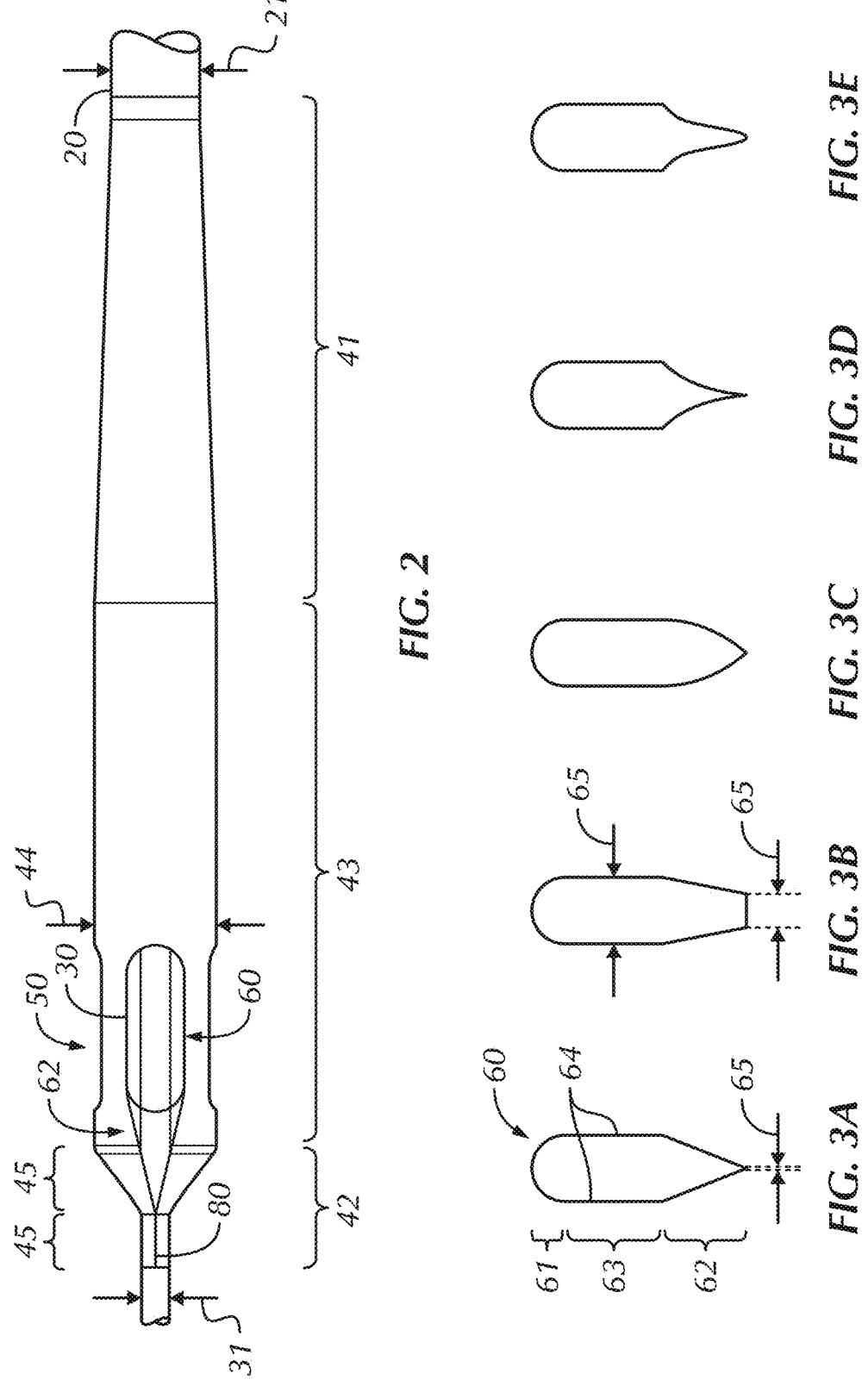
FIG. 2 is an illustration of a top view of the flexible outflow cannula.
FIGS. 3A-3E are illustrations of top views of cut outlets.

Referring to FIG. 2, a top view of flexible outflow cannula can be seen. In preferred embodiments, the flexible outflow cannula may be defined by a substantially tubular member having a sidewall thickness of less than 20 microns. In some embodiments, sidewall thickness may be 30 microns or less. In some embodiments, sidewall thickness may be 18 microns or less. In some embodiments, sidewall thickness may be 17 microns or less. In some embodiments, sidewall thickness may be 16 microns or less. In some embodiments, sidewall thickness may be 15 microns or less. In some embodiments, sidewall thickness may be 10 microns or less. As seen, in some embodiments, the catheter 30 may have an outer diameter 31 that may be smaller than an outer diameter 21 of the pump housing 20.

In some embodiments, the flexible outflow cannula may include an intermediate portion 43 extending between the distal portion 41 and the proximal portion 42. The intermediate portion may have an outer diameter 44 larger than the outer diameter 21 of the pump housing.

The proximal portion 42 of the flexible outflow cannula may have a coupled portion 45 coupled to the catheter 30 and an uncoupled portion 46 extending distally from the coupled portion.

At least one slit 80 may be formed through the entire coupled portion 45 and extending to a proximal end of the flexible outflow cannula.

As used here, a "slit" refers to a division or opening between adjacent parts of the coupled portion that are (or have been) divided in some fashion (e.g., using a laser, a cutting die, scissors, etc.). There may be some separation or volume of empty space between the two adjacent parts. The two adjacent parts may overlap. The two adjacent parts may otherwise be connected such that there is no separation or volume of space separating the adjacent parts. In some embodiments, the two adjacent parts are separated by a distance greater than 1 micron. In some embodiments, the two adjacent parts are separated by a distance less than 1 micron. In some embodiments, the two adjacent parts abut each other.

In some embodiments, only a single slit may be present. In some embodiments, two slits may be present. In some embodiments, if two slits are present, they may be located on opposite sides of the outflow cannula (e.g., located 180 degrees, around a central axis of the outflow cannula).

In some embodiments, the blood flow outlets 50, 60 may include one or more cut outlets 60, and the slit may connect to a proximal end of at least one of the cut outlets. In some embodiments, the slit may connect to the proximal end of the cut outlet 60 at the proximal end of the uncoupled portion 46. In some embodiments, the slit may extend distally from the coupled portion through at least a portion of the uncoupled portion and connects to a proximal end of a cut outlet.

The cut outlets may extend distally from the uncoupled portion and may have a tapered proximal portion 62.

In some embodiments, the plurality of blood flow outlets consists of four blood flow outlets 50, 60 and the cut outlets 60 consists of one or two of those four outlets. In some embodiments, the plurality of blood flow outlets may include four blood flow outlets 50, 60, of which only one may be a cut outlet 60. In some embodiments, each of the plurality of blood flow outlets 50, 60 may be spaced equally distant circumferentially from adjacent blood flow outlets. That is, if there are three outlets, the centerline (e.g., an imaginary line extending from the proximal end to the distal end of each outlet that bisects the cross-sectional area of the outlet) of each outlet may be offset adjacent outlets by 120 degrees. If there are four outlets, the centerlines may be offset by 90 degrees, five outlets may have a 72-degree offset, and so on.

In some embodiments, each of the plurality of blood flow outlets 50, 60 may be positioned at least partially in the intermediate portion 43 of the outflow cannula, and only the cut outlets 60 are positioned at least partially in both the proximal portion 42 of the outflow cannula and the intermediate portion 42 of the outflow cannula.

Referring to FIG. 3A, in some embodiments, each cut outlet may include a distal portion 61 and a proximal portion 62. Each cut outlet may include an intermediate portion 63 between the distal portion and proximal portion. In some embodiments, the intermediate portion may have substantially parallel sides 64.

The shape of the proximal portion may vary. For example, in some embodiments, the proximal portion 62 may form a cut with straight but non-parallel sides (FIGS. 3A and 3B).

In some embodiments, the non-parallel sides form a V-shaped cut (see FIG. 3A). In some embodiment, the width 65 of the cut at the proximal end may be equal to the width of the slit 80 that connects to the cut. In some embodiment, the width 65 of the cut at the proximal end may be less than the width of the slit 80 that connects to the cut. In some embodiment, the width 65 of the cut at the proximal end may be no more than 1 mm. In some embodiment, the width 65 of the cut at the proximal end may be no more than 500 microns. In some embodiment, the width 65 of the cut at the proximal end may be no more than 250 microns. In some embodiment, the width 65 of the cut at the proximal end may be no more than 125 microns. In some embodiment, the width 65 of the cut at the proximal end may be no more than 50 microns. In some embodiment, the width 65 of the cut at the proximal end may be no more than 25 microns. In some embodiment, the width 65 of the cut at the proximal end may be no more than 10 microns.

In some embodiments, the non-parallel sides may form a trapezoidal shaped cut (see FIG. 3B). In some embodiments, the width 65 of the cut at the proximal end may be greater than the width of the slit 80, but less than a width 66 of the intermediate portion 63 of the cut. In some embodiments, the proximal portion may form a cut with concave sides (see FIG. 3C). In some embodiments, the proximal portion may form a cut with convex sides (see FIGS. 3D, 3E).

In some embodiments, the proximal end of the cut may substantially come to a point (FIGS. 3A, 3C, 3D). In some embodiments, the proximal end of the cut may be a squared or flattened end (FIG. 3B). In some embodiments, the proximal end of the cut may be rounded (FIG. 3E).

Referring to FIG. 4A, in some embodiments, the slit 80 may be configured to allow at least a first portion 47 of the coupled portion 45 to overlap a second portion 48 of the coupled portion. Referring to FIG. 4B, in some embodiments, the slit 80 may be configured to prevent a first portion of the coupled portion of the proximal end portion from overlapping with a second portion of the coupled portion of the proximal end portion.

In some embodiments, the pump housing, the impeller, and any filter may each alternatingly radially compressible and radially expandable.

Figure 5:
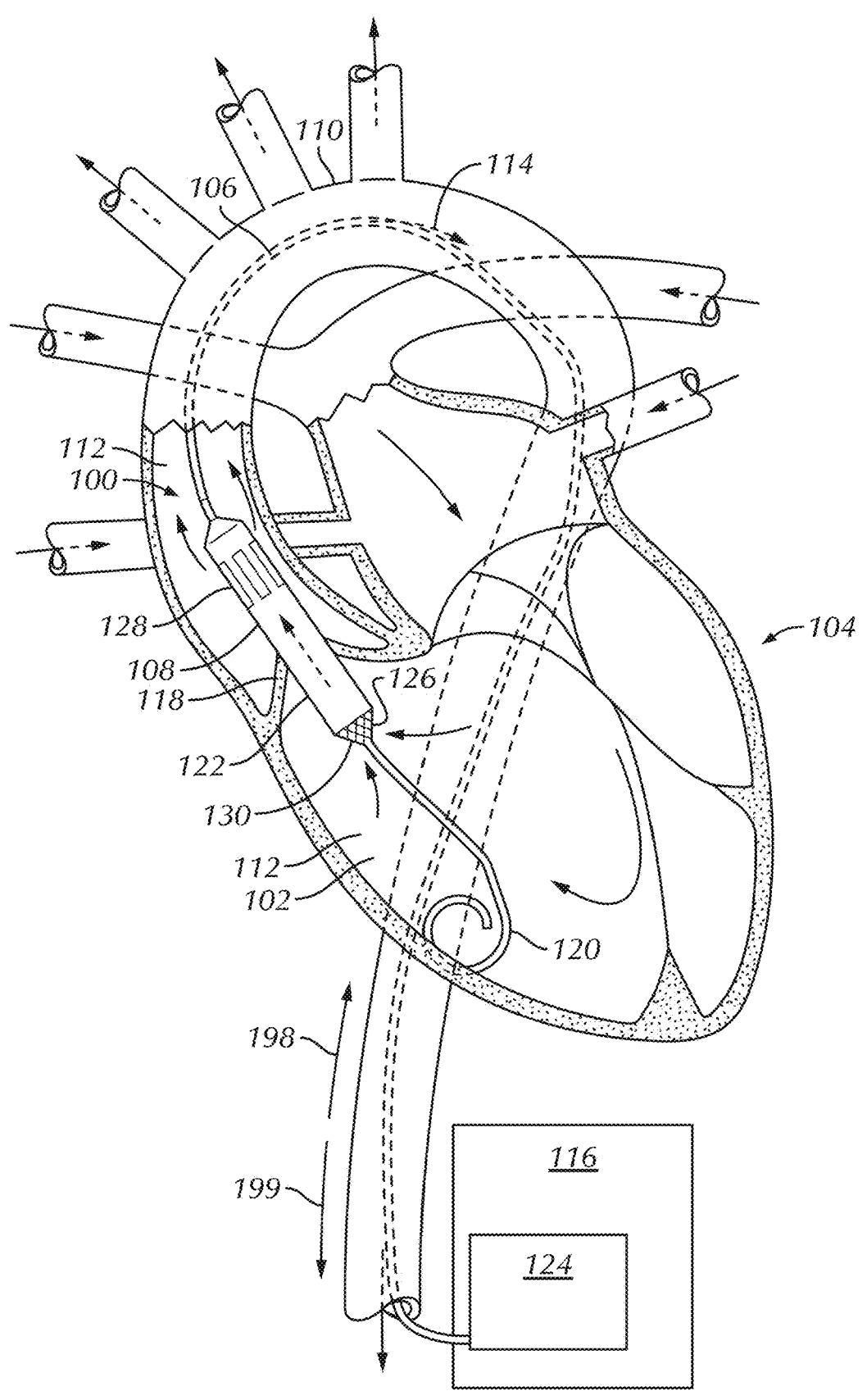
FIG. 5 is a partial cut-away illustration of a blood pump positioned within a left ventricle of a heart.

FIG. 5 is a partial cut-away illustration of an expandable blood pump 100 positioned within a left ventricle 102 of a heart 104 of a patient, although in other uses, the expandable blood pump 100 may be positioned elsewhere in the patient, such as in the left atrium or elsewhere in the patient's vasculature, not necessarily in the heart 104. The blood pump 100 may include a catheter 106 and a pump section 108 disposed at or near the end of the catheter 106.

The catheter 106 may be configured for insertion into a blood vessel, such as the aorta 110, that defines an interior volume 112, through which blood flows in a blood flow direction 114, the exemplary direction indicated here by an arrow. As used herein, the term "blood vessel" includes a heart chamber or other lumen. The catheter 106 may be connected to a controller 116, such as an Automatic Impella Controller ("AIC") available from Abiomed, Inc. The controller 116 may provide a user interface for controlling and monitoring the intravascular blood pump 100.

As used herein, the term "distal" refers to a direction or location along the catheter 106 away from the controller 116 or user of the controller 116, and the term "proximal" refers to a direction or location along the catheter 106 toward the controller 116 or user of the controller 116, as indicated by arrows (distal 198, proximal 199) in FIG. 5.

During insertion, the intravascular blood pump 100 may be positioned to extend through the aortic valve 118, as shown in FIG. 5, although in other uses the intravascular blood pump 100 may be positioned elsewhere in a patient's vasculature, not necessarily in the heart 104. Furthermore, although FIG. 5 depicts the intravascular blood pump 100 inserted such that the blood flow direction 114 may be away from the distal end of the catheter 106, in other uses the intravascular blood pump 100 may be inserted such that the blood flow direction 114 may be toward the distal end of the catheter 106. For example, the intravascular blood pump 100 may be inserted from the left atrium, through the mitral valve, into the left ventricle 102. In the use depicted in FIG. 5, leaves of the aortic valve 118 close around the intravascular blood pump 100.

The intravascular blood pump 100 may be placed inside the heart 104 using a percutaneous, transluminal technique. For example, the intravascular blood pump 100 may be introduced through a femoral artery (not shown). However, alternative vascular access may be equally possible, such as access through the subclavian artery. After passing through the femoral artery, the catheter 106 may be pushed into the aorta 110, such that the pump section 108 reaches through the aortic valve 118 into the heart 104. The positioning of the pump section 108 in FIG. 1 serves purely as an example, whereas different placements are possible, such as positioning the pump section 108 inside the right ventricle of the heart 104.

A flexible atraumatic tip 120 having, for example, the form of a pigtail or a J-form extends distally from the pump section 108 distal end. The atraumatic tip 120 should be sufficiently soft to allow the pump section 108 to support itself atraumatically against the inside wall of the left ventricle 102.

The pump section 108 includes an impeller (not visible) disposed inside a housing 122. The housing 122 and the impeller can, but need not necessarily, be expandable. The impeller may be mechanically coupled, via a flexible drive shaft (ref. 202, not shown in this figure) that extends through the catheter 106, to an external motor 124. The motor 124 may be in the controller 116 or elsewhere. Alternatively, the impeller may be mechanically coupled via a relatively short drive shaft (not shown) to a motor (not shown) disposed in the pump section 108. In either case, the motor rotates the impeller, via the drive shaft, to cause blood from the interior volume 112 to flow from a blood flow inlet (input port) 126 at a distal end of the pump section 108 to a blood flow outlet (output port) 128 located proximal of the blood flow inlet 126, as indicated by arrows. As noted, the term "interior volume" 112 includes a heart chamber, such as the left ventricle 102.

A filter 130 may be disposed in fluid communication between: (a) the interior volume 112 of a blood vessel, in this case the left ventricle 102, external to the pump housing 122, and (b) the input port 126. Although the filter 130 is described in relation to an expandable housing 122 and impeller, the filter 130 may also be used with a non-expandable housing 122 and impeller.

Figure 6:
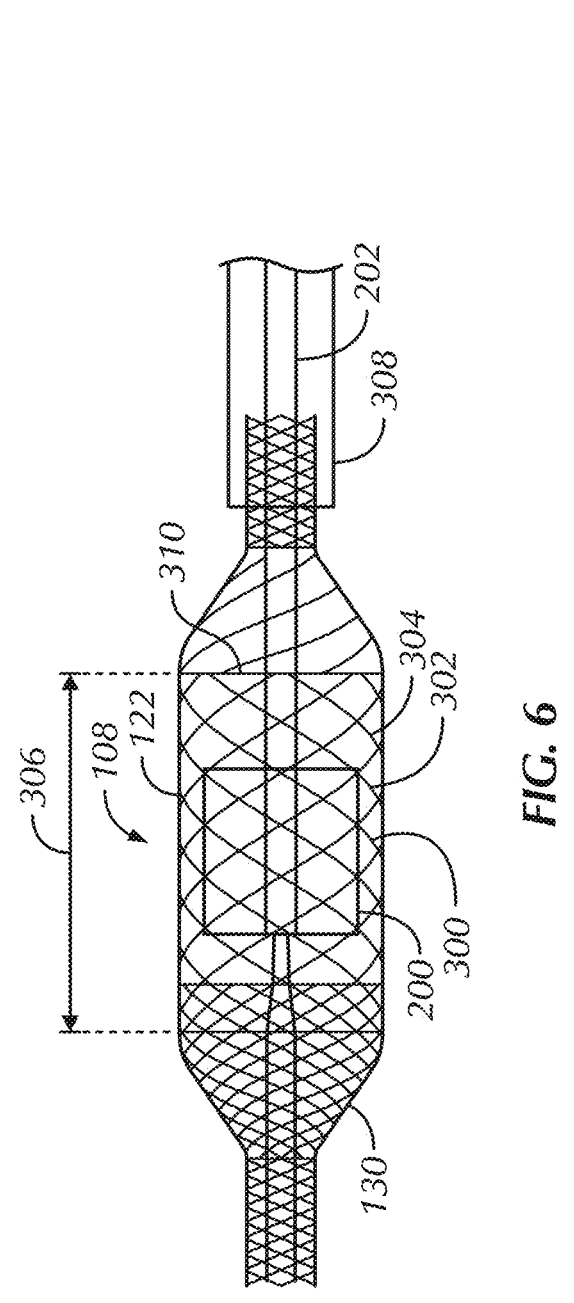
FIGS. 6-7 are enlarged side cut-away views of an expandable housing of the intravascular blood pump of FIGS. 1 and 5, as well as an expandable mesh filter, in an expanded state (FIG. 6) and in a compressed state (FIG. 7), respectively.
Figure 7:
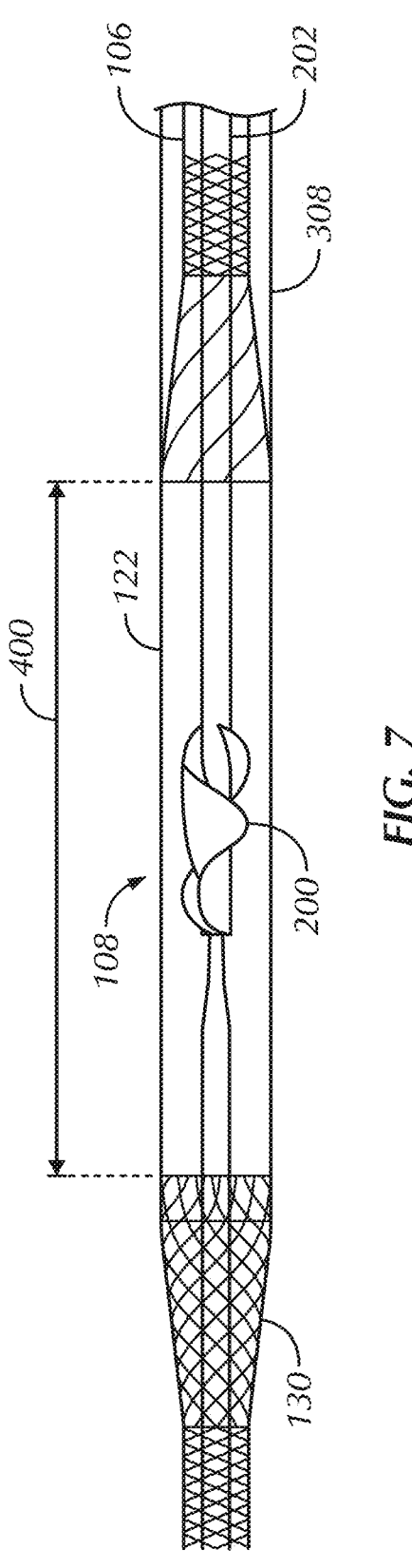

The struts 300-304 that are used in the filter may be made of wire or other filament. As shown in FIGS. 6 and 7, the housing 122 may provide a cage around the impeller 200. When radially expanded (FIG. 6), the length 306 of the housing 122 may be less than the length 400 when the housing 122 may be radially compressed (FIG. 7). The change in length 400 to 306 may be due to unwinding of the struts 300-304, when the housing 122 expands. In some embodiments, the change in length 400 to 306 may be about 1-2 mm.

The expandable housing 122, expandable impeller 200 and expandable filter 130 may be kept in their compressed states by a suitable compression sleeve 308 slid over the expandable housing 122, expandable impeller 200 and expandable filter 130. The intravascular blood pump 100, with the expandable housing 122, expandable impeller 200 and expandable filter 130, may be transported through the patient's vascular system while the housing 122, impeller 200 and filter 130 are in their compressed states. Once the pump section 108 is at its target location, the housing 122, the impeller 200 and the filter 130 may be allowed to expand, e.g., by pushing the pump section 108 out of the compression sleeve 308 in a forward (distal) direction or by pulling back (in a proximal direction) the compression sleeve 308. With the compression sleeve 308 removed, the housing 122 expands, due to its shape-memory, superelastic or hyperelastic properties, as shown in FIG. 6. At the same time, the impeller 200 expands due to its elasticity. As the housing 122 expands radially away from the drive shaft 202, the housing 122 may longitudinally contract to the length 306.

An inside central portion of the housing 122 may have a sleeve or coating 310 (best seen in FIG. 14), which defines a channel, through which the blood may be pumped by the impeller 200. Proximally and distally of this channel, the housing 122 may allow blood to be drawn into the housing 122 and pushed out of the housing 122 into the outflow cannula respectively.

When the intravascular blood pump 100 may be in its expanded state and needs to be removed from the patient, the housing 122 may be pulled back into the compression cannula 308, which causes the housing 122 to compress radially, and may cause the housing 122 to longitudinally extend to the length 400. The filter 130 and the impeller 200 may also be compressed. The smaller diameter of the housing 122 thus achieved facilitates removing the intravascular blood pump 100 from the patient through the vasculature. Thus, the pump housing 122, the impeller 200 and the filter 130 are each configured to be alternatingly radially compressed and radially expanded. Additional details of an expandable intravascular blood pump are provided in U.S. Pat. No. 8,439,859, the entire contents of which is hereby incorporated by reference herein, for all purposes.

Figure 8:
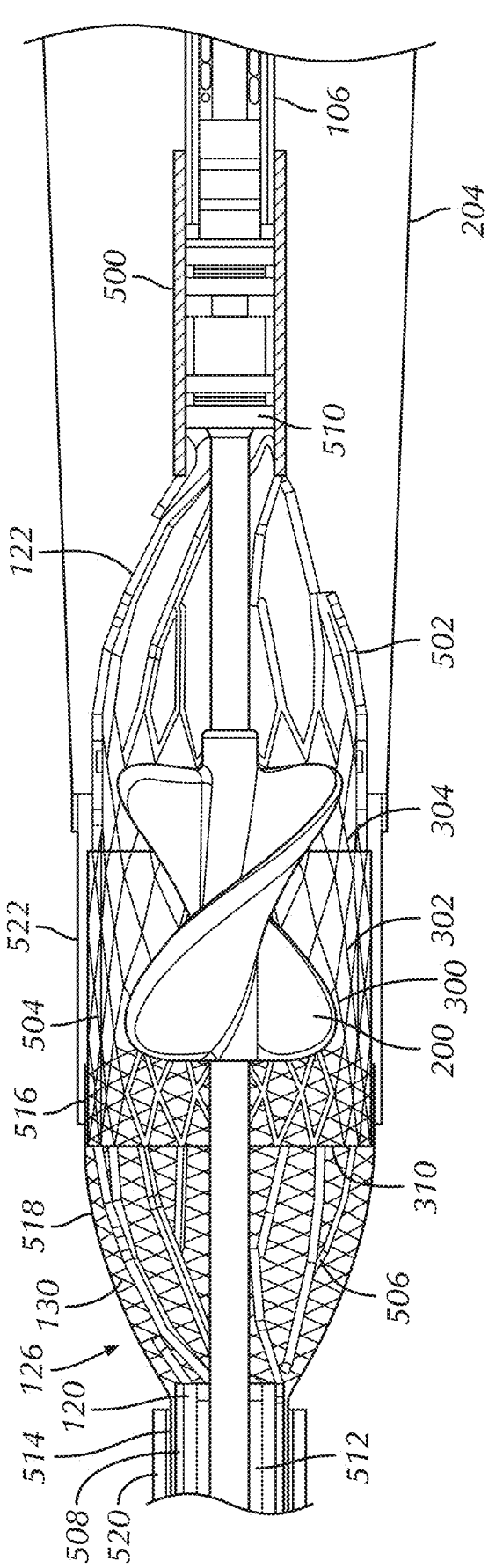
FIG. 8 is a cross-sectional view of the expandable housing and expandable mesh filter of FIG. 6 in the expanded state, according to an embodiment of the present invention.

FIG. 8 is a cross-sectional view of the expandable housing 122 and expandable mesh filter 130 of FIGS. 6 and 7 in their expanded states. The housing 122 includes several parts connected to each other. These parts are, proximally to distally: a proximal tubular housing part 500, a proximal tapered housing part 502, an intermediate tubular housing part 504, a distal tapered housing part 506 and a distal tubular housing part 508. As used herein, "tapered" means having a shape that changes outer diameter smoothly and monotonically, but not necessarily linearly. Thus, in profile, a tapered shape may include convex and/or concave portions. Tapered includes, but is not limited to, conical.

The proximal tubular housing part 500 may be attached to the catheter 106 and contains a proximal bearing 510. The proximal tubular housing part 500 has an essentially cylindrical shape. The proximal tapered housing part 502 connects the intermediate tubular housing part 504 to the proximal tubular housing part 500. The intermediate tubular housing part 504 has an approximately cylindrical shape and surrounds the impeller 200. The exact cross-sectional shape of the intermediate tubular housing part 504 may depend on the number of struts 300-304 in the housing 122. In general, the cross-sectional shape may be a polygon, possibly with rounded corners.

The distal tapered housing part 506 connects the intermediate tubular housing part 504 to the distal tubular housing part 508 and defines the blood flow inlet (inlet port) 126 of the housing 122. The proximal tapered housing part 502 has a nearly circular cross-section whose radius increases in the distal direction. As with the intermediate tubular housing part 504, the exact cross-sectional shape of the proximal tapered housing part 502 may depend on a number of struts 300-304 and, in general, the cross-sectional shape may be a polygon, possibly with rounded corners.

Similarly, the distal tapered housing part 506 also has a nearly circular cross-section whose radius, however, decreases in the distal direction. As with the intermediate tubular housing part 504, the exact cross-sectional shape of the distal tapered housing part 506 may depend on a number of struts 300-304 and, in general, the cross-sectional shape may be a polygon, possibly with rounded corners.

The distal tubular housing part 508 contains a distal bearing 512 and may be connected to a proximal section of the flexible atraumatic tip 120.

Expandable Filter

Mounted on the outside of the expanded housing 122 and, thus, shown in its expanded state, may be the expandable filter 130. The filter 130 may include a distal tubular filter section 514, which has a relatively small diameter. The filter may include a proximal tubular filter section 516, which has a larger diameter. As with the intermediate tubular housing part 504, the exact cross-sectional shape of the filter 130, including the exact cross-sectional shape of the distal tubular filter section 514 and the proximal tubular filter section 516, may depend on a number of struts 300-304 and/or a number of struts in the filter 130. In general, the cross-sectional shape may be a polygon, possibly with rounded corners.

A tapered filter section 518 may connect the two tubular filter sections 516 and 514. The expandable filter 130 may cover the entire distal tapered housing part 506, i.e., the blood flow inlet (input port) 126, with its tapered filter section 518. The expandable filter may cover some of the intermediate tubular housing part 504 with its proximal tubular filter section 516. In some embodiments, the expandable filter may cover some, but not all, of the distal tubular housing part 508 with its distal tubular filter section 514. In some embodiments, the expandable filter may cover all of the distal tubular housing part 508 with its distal tubular filter section 514.

A distal outer foil 520 may be arranged on top of the distal tubular filter section 514. The distal tubular filter section 514 may be arranged on top of the distal tubular housing part 508. The distal outer foil 520 (or film) may prevent damage to the expandable filter 130. For example, the foil may prevent fraying if the expandable filter 130 is made of a mesh of struts. If the distal tubular filter section 514 defines apertures, the distal outer foil 520 may be attached directly to the structure situated underneath the distal tubular filter section 514, such as the flexible atraumatic tip 120, via the apertures. For example, the flexible atraumatic tip 120 and the distal outer foil 520 may be made from the same or similar materials, and the materials may be welded together via the apertures. Since the flexible atraumatic tip 120 may typically be made of Polyether block amide (PEBA) or polyurethane, the distal outer foil 520 may also be made of PEBA or polyurethane, and the materials may be heat sealed together.

A proximal outer foil 522 may be disposed on top of the intermediate tubular housing part 504. The proximal tubular section 516 of the expandable filter 130 may be sandwiched between the proximal outer foil 522 and the intermediate tubular housing part 504, albeit only at a distal region of the proximal outer foil 522. The proximal outer foil 522 may prevent damage to the proximal tubular section 516 of the expandable filter 130. In addition, the proximal outer foil 522 may be heat sealed to the inside sleeve or coating 310 of the housing 122 through the apertures in the expandable filter 130. The inside sleeve or coating 310 may be made from polyurethane (PU). When the inside sleeve or coating 310 is made of PU, the proximal outer foil 522 may preferably likewise be made of PU. When the filter 130 is made with a shaped foil tube that defines apertures, the proximal outer foil 522 may be made integral with the filter 130.

The distal end of the flexible outflow cannula 204 may be attached to a proximal section of the proximal outer foil 522. Alternatively, the flexible outflow cannula 204 may be made integral with the proximal outer foil 522. When the filter 130 is made with a shaped foil tube that defines apertures, the proximal outer foil 522 may be made integral with the filter 130 and the flexible outflow cannula 204.

Helically Woven Filaments Filter

Figure 9:
FIG. 9 shows is a perspective view of an expandable filter formed of a mesh of filaments and mounted on a distal end region of the expandable housing (FIGS. 6-8) of the intravascular blood pump of FIGS. 1-5, according to an embodiment of the present invention.

FIG. 9 contains a perspective view of a distal section of the intravascular blood pump 100 with the intermediate tubular housing part 504, the distal tapered housing part 506 and the distal tubular housing part 508. In this embodiment, the expandable filter 130 may be a mesh made of filaments that are woven or connected to each other. Weaving is a method of production in which two distinct sets of filaments (warp and weft) are interlaced at angles to form a fabric. The warp is made up of longitudinal filaments, and the weft (or filling) is made up of lateral filaments. The way the warp and weft filaments interlace with each other is called the weave. The majority of woven products are created with one of three basic weaves: plain weave, satin weave or twill.

In plain weave, the warp and weft filaments cross at angles, aligned so they form a simple crisscross pattern. Each weft filament crosses the warp filaments by going over one, then under the next, and so on. The next weft filament goes under the warp threads that its neighbor went over, and vice versa. The filaments of a woven filter 130 are preferably plain woven, although satin, twill or other weaves may be used. Preferably, the mesh is not knitted and contains no loops.

The satin weave may be characterized by four or more weft filaments floating over a warp filament, and four or more warp filaments floating over a single weft filament. Floats are missed interfacings, for example where the warp filament lies on top of the weft filaments in a warp-faced satin. The twill weave may be characterized by a pattern of diagonal parallel ribs. Twill weave may be made by passing the weft filament over one or more warp filaments, then under two or more warp filaments, and so on, with a "step," or offset, between rows to create a characteristic diagonal pattern.

Figure 10:
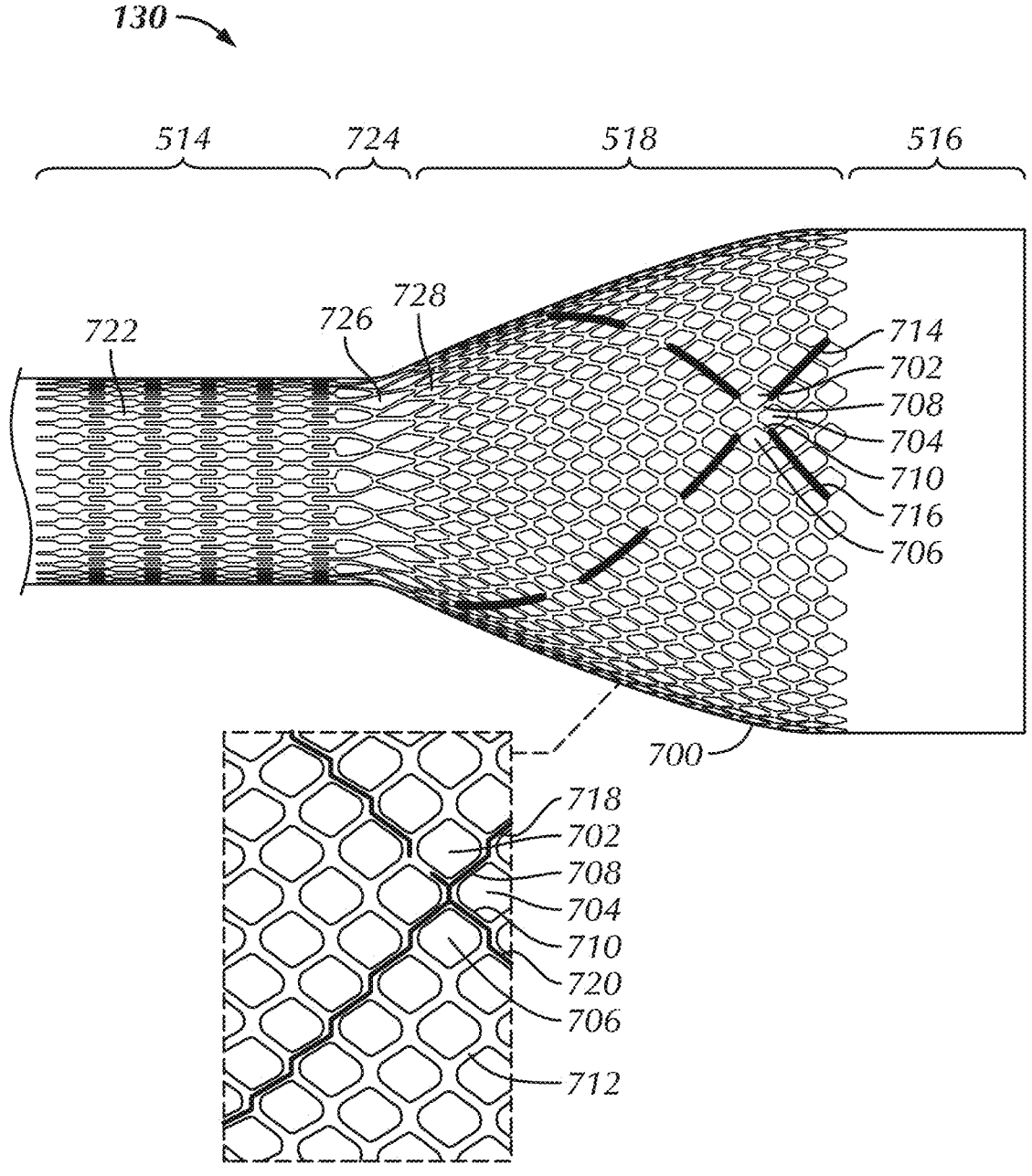
FIG. 10 is a side view, of the expandable filter formed of a filter tube, according to another embodiment of the present invention.

Referring to FIG. 9, the filter 130 may be made of filaments, represented by filaments 600, 602, 604, 608, 610, 612, 614, 616 and 618. The filaments 600-608 are generally helical first struts wound clockwise about a longitudinal axis 620 of the housing 122. As used herein, a "generally helical" curve is a generally smooth space curve. However, as used herein, pitch, radius, curvature and torsion may vary along the length of a helical curve. A helical curve may, but need not, wind more or less than 360° around an axis. Furthermore, a generally helical curve may include minor zigzags, not necessarily all the same, as exemplified by the generally helical curves 714 and 716 (FIG. 10).

Returning to FIG. 9, the filaments 610-618 may be generally helical second struts wound counterclockwise about the longitudinal axis 620. The filaments 600-618 are indicated by heavy dashed lines, to make them easier to see in the drawing. These filaments 600-618 are also reproduced in an insert in FIG. 9, for clarity. The first struts 600-608 and the second struts 610-618 collectively define a plurality of apertures therebetween, represented by apertures 622, 624 and 626. The first struts 600-608 and the second struts 610-618 are woven together, such that the plurality of apertures 622-626 is defined between respective adjacent first and second woven filaments 600-618.

Each aperture of at least a subset of the plurality of apertures 622-626 may have a general rhombus or rhomboid or rectangular shape. As used herein, a rhomboid is a parallelogram in which adjacent sides are of unequal lengths and angles between adjacent sides are non-right angles. As used herein, a rhombus is a parallelogram in which adjacent sides are equal lengths and angles between adjacent sides are non-right angles. Rhomboids, rhombi and rectangles are not necessarily planar. Rhomboids, rhombi and rectangles may exist on curved surfaces, as exemplified by apertures 622-626. The sides of a rhomboid, a rhombus or a rectangle need not be perfectly straight, and the sides need not necessarily meet at corners, i.e., there may be a small radius where the two sides meet, for example as discussed in more detail below, with respect to corners in apertures defined by shaped foil tube filters.

In at least a middle portion 628 of the tapered filter section 518, the apertures 622-626 may be preferably approximately square shaped. As the diameter of the filter 130 decreases, such as in the distal direction within the tapered filter section 518, the apertures 622-626 may become progressively smaller, and the apertures may become rhomboid shaped, with their long axes extending longitudinally. At the smallest diameter of the tapered filter section 518, the smaller inner angles of rhombus or rhomboid apertures may be less than about 75°.

As the diameter of the filter 130 increases, such as in the proximal direction within the tapered filter section 518, the apertures 622-626 may become progressively larger. At the largest diameter of the tapered filter section 518, the larger inner angles of rhombus or rhomboid apertures may be greater than about 110°. The apertures may become rhomboid shaped, with their long axes extending circumferentially. These numbers correspond to an embodiment in which the larger diameter of the filter 130 is about 2.5 times the smaller diameter of the filter 130. For other ratios of large to small diameters of filter 130, the angles can be adjusted.

The pump housing 122 may be configured, when radially compressed, to longitudinally lengthen an amount that depends on an amount by which the pump housing 122 is radially compressed. The filter 130 may be configured, when radially compressed, to longitudinally lengthen an amount that depends on an amount by which the filter 130 is radially compressed. The filter 130 may be configured such that, for a given amount of radial compression, the filter 130 and the pump housing 122 longitudinally lengthen about equal amounts.

The filaments 600-618 may be a wire, such as Nitinol, suitable polymer, such as polyethylene terephthalate (PET) or PU, fiber or another suitable material. The filament 600-618 material is preferably a shape memory material. Individual filaments 600-618 may have a thickness of between about 10 μm and about 80 μm, or between about 20 μm and about 60 μm, such as about 40 μm. The catheter 106, the pump housing 122, the impeller 200 and the filter 130 are configured for use in a living patient, such that each aperture of the plurality of apertures 622-626 is sized to prevent ingestion, by the input port 126, of heart tissue of the living patient.

In some embodiments where the filter 130 is formed of a mesh, the mesh may be ironed (pressed under heat), prior to attaching the filter 130 to the housing 122. Such ironing may fuse crossing filaments 600-618, particularly if the filaments 600-618 are made of a suitable heat-fusible plastic. Such fused filaments 600-618 form a stronger mesh.

In some embodiments, the woven fabric has a maximum distance between two adjacent filaments 600-618 of between about 0.3 mm (300 μm) and about 0.4 mm (400 μm), when the filter 130 is in the expanded state. In some embodiments, each aperture of the plurality of apertures 622-626 has a largest dimension less than or equal to about 0.5 mm (500 μm), when the filter 130 is in the expanded state. In some embodiments, each aperture of the plurality of apertures 622-626 has a largest dimension less than or equal to about 0.4 mm (400 μm), when the filter 130 is in the expanded state. In some embodiments, each aperture of the plurality of apertures 622-626 has an area less than or equal to about 0.09 mm2, when the filter 130 is in the expanded state. In some embodiments, each aperture of the plurality of apertures 622-626 has an area less than or equal to about 0.16 mm2, when the filter 130 is in the expanded state.

As used herein, "largest dimension" includes a diagonal dimension, such as a dimension between two diagonally opposite corners of a quadrilateral. As used herein, "diameter" of a convex shape means a largest distance that can be formed between two opposite parallel lines tangent to the boundary of the convex shape. As used herein, "width" means the smallest such distance.

Shaped Foil Tube Filter

Figure 11:
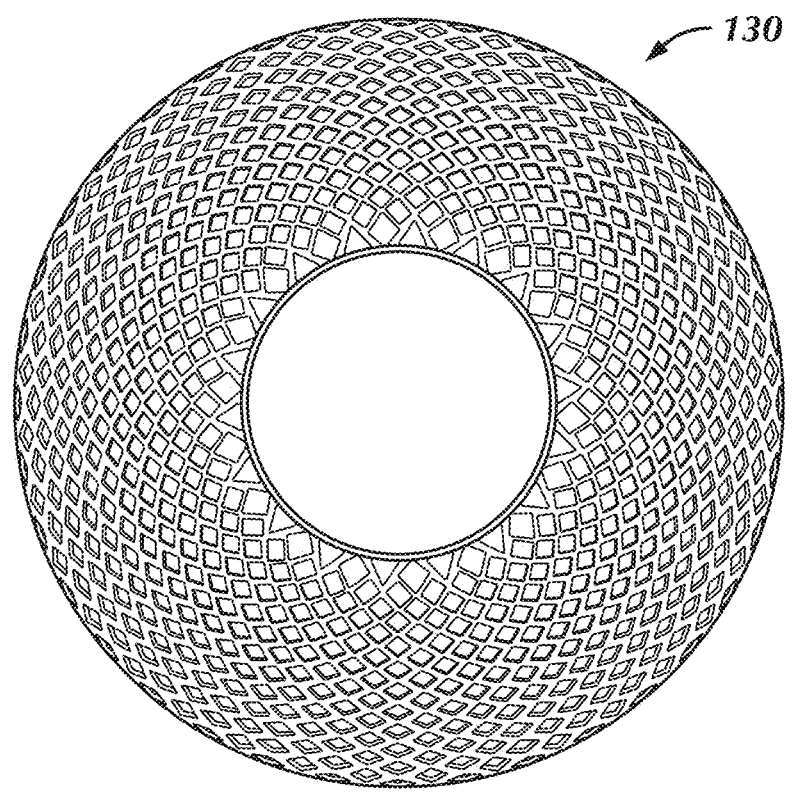
FIG. 11 is an axial (longitudinal) view, of the expandable filter formed of a filter tube, according to another embodiment of the present invention.

FIG. 10 is a side view, and FIG. 11 is an axial (longitudinal) view, of an expandable filter 130 formed of a filter tube. In some embodiments, the tube may be a generally funnel-shaped tube. FIG. 10 includes an insert showing an enlarged portion of the expandable filter 130. As noted, in some embodiments, the filter 130 includes a shaped foil tube 700 with the apertures. The apertures may be openings through a wall forming the tube. The wall may be, e.g., 10-100 μm thick. Examples of the apertures are shown at 702, 704 and 706. An expandable filter 130 made from a shaped foil tube 700 may be compressed, i.e., radially made smaller, by folding some or all parts of the filter 130. The filter 130 may be expanded from its compressed state by unfolding the previously folded parts. Compression and expansion rely primarily on this folding and unfolding, rather than on elastic compression and elongation.

The apertures 702-706 may be positioned on the tube, such that material, exemplified by material 708, 710 and 712, between the apertures 702-706 forms first and second struts. Two exemplary struts 714 and 716 are indicated in FIG. 10 by heavy dashed lines. As noted, a generally helical curve may include minor zigzags, not necessarily all the same, as exemplified by generally helical curves 714 and 716. These zigzags are more clearly seen in the insert in FIG. 10, for example in struts 718 and 720, which are indicated by heavy solid and dashed lines.

FIGS. 10 and 11 show the expanded filter 130 as the filter 130 appears when mounted on an expanded housing 122 (e.g., FIG. 9), although the housing 122 is not shown in FIGS. 10 and 11. A filter 130 made of a shaped foil tube 700 may be made of a polymer, such as PET or PU. The wall of the foil tube 700 may be about 10 μm to about 100 μm thick, preferably about 15 μm to about 75 μm thick, and more preferably about 20 μm to about 50 μm thick. The thickness of the foil tube 700 wall may decrease continuously in a distal direction in the tapered filter section 518, such as a result of blow mold manufacturing.

Figure 12:
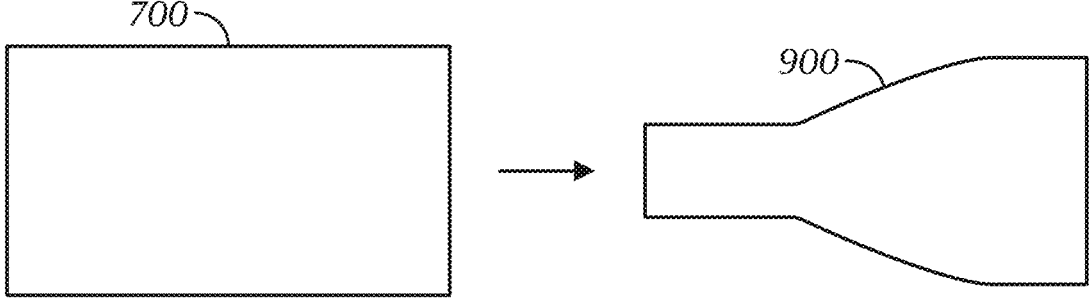
FIG. 12 is a side view illustration of a method for shaping the filter tube of FIGS. 10 and 11, according to an embodiment of the present invention.

As shown in FIG. 12, the foil tube 700 may be shaped on a mandrel 900. The mandrel 900 should have the desired shape of the finished filter 130 in the expanded state. The apertures 702-706 can then be defined in the shaped tube, such as by cutting or punching. The apertures 702-706 may have a general rhombus or rhomboid or rectangular shape. The inside corners of apertures 702-706 in foil tube 700 based filters 130 should have radii of at least about 5 and preferably at least about 20 μm.

Figure 13:
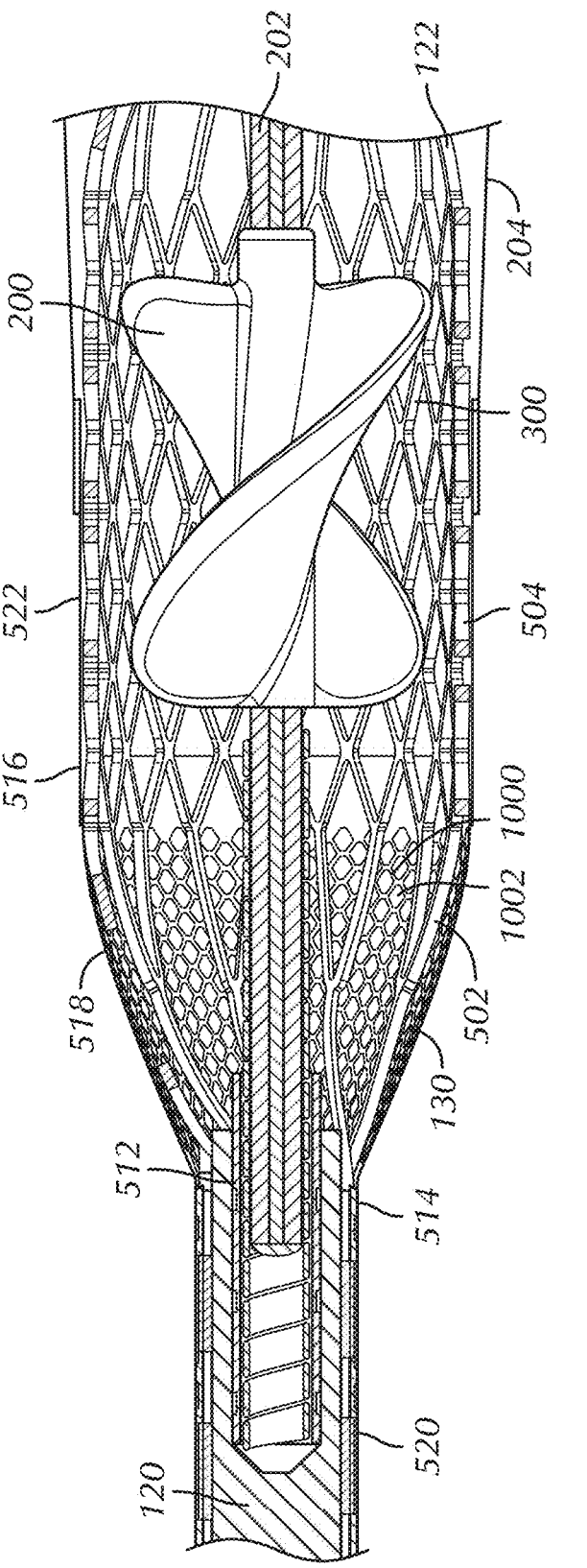
FIG. 13 is a cross-sectional view of the distal end region of the expandable housing of FIGS. 6-8, with the expandable filter of FIGS. 10 and 11 installed thereon, according to an embodiment of the present invention.
Figure 14:
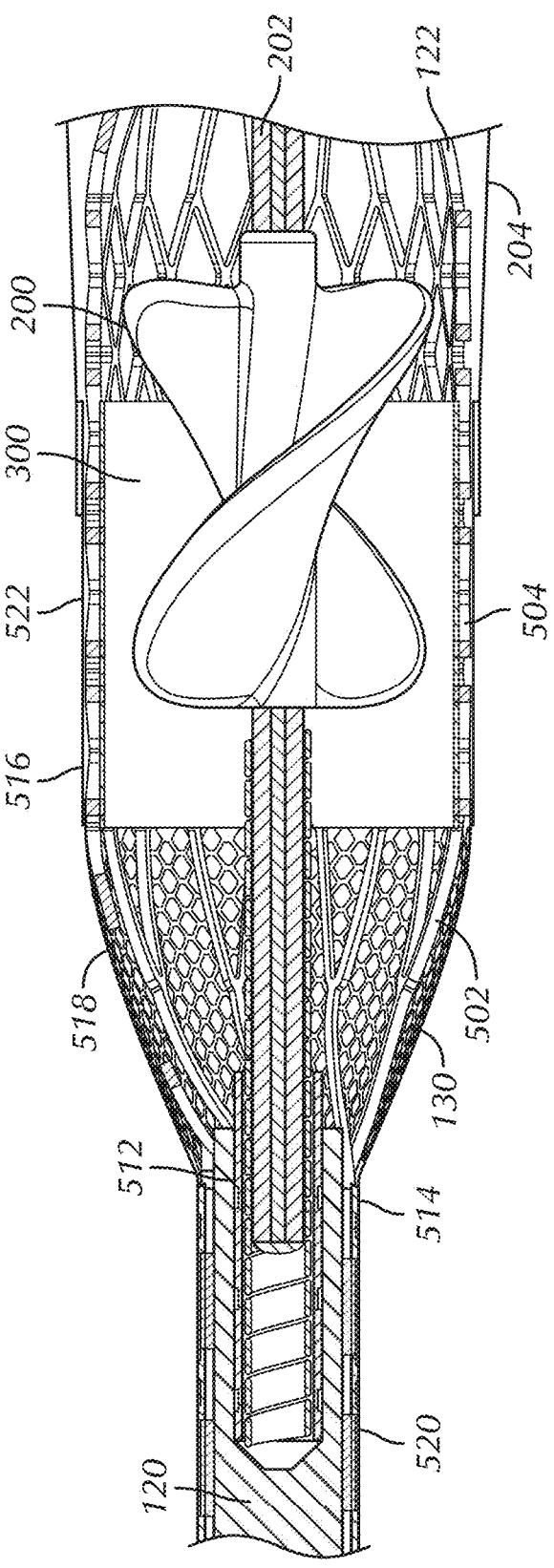
FIG. 14 is a cross-sectional view, as in FIG. 13, however including an expandable housing inner coating, which is not shown in FIG. 13 for clarity.
Figure 15:
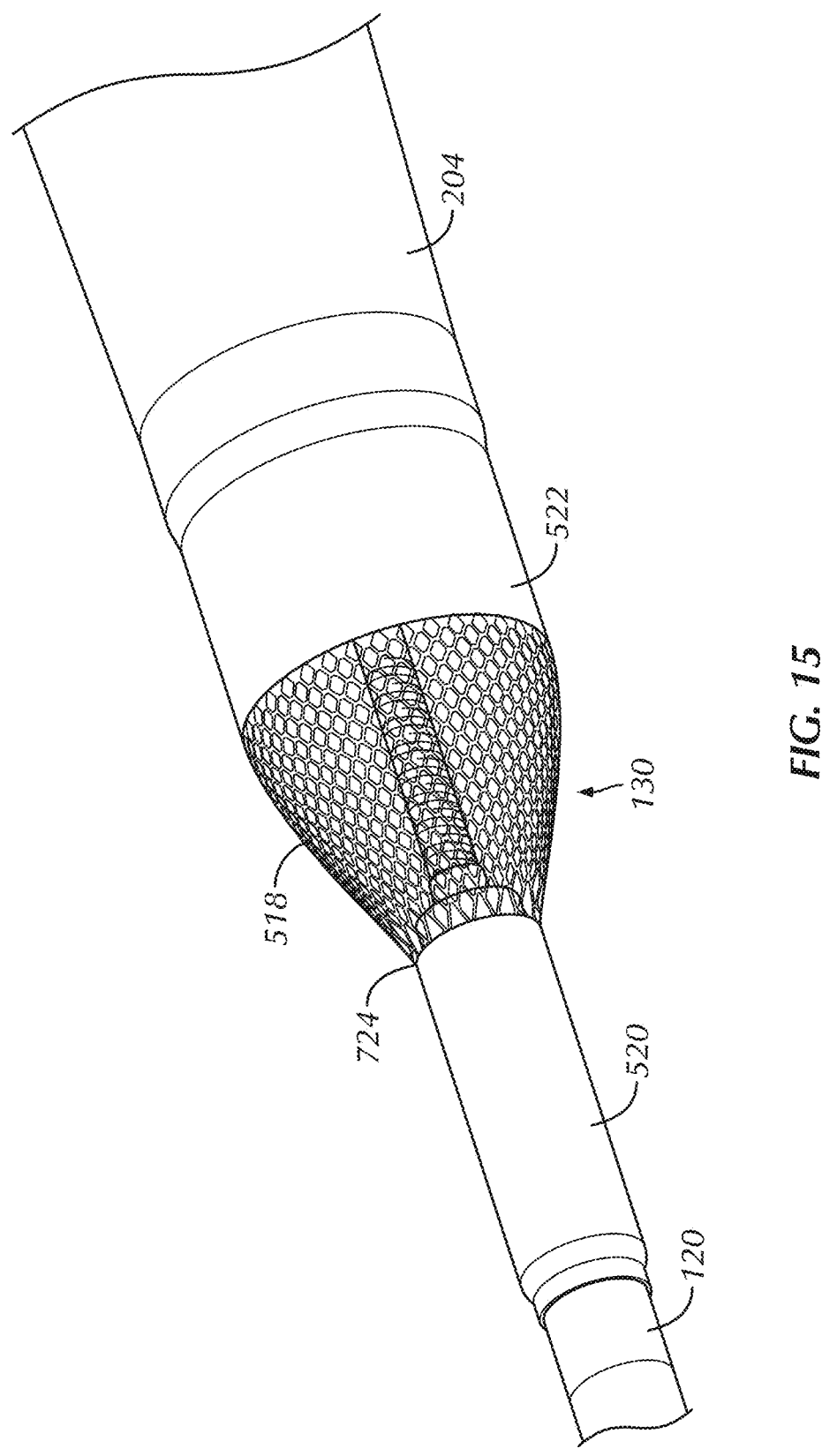
FIG. 15 is a perspective view of the distal end region of the expandable housing of FIGS. 13-14, with the expandable filter of FIGS. 10-12 installed thereon.

Additional holes may be defined in the shaped tube, such as to facilitate attaching the shaped tube to other components of the intravascular blood pump 100, as discussed herein. The shaped apertured tube can then be installed on the housing 122, as shown in FIGS. 13-15 (The housing 122 is not visible in FIG. 15.). FIG. 13 is a cross-sectional view of the distal end region of the expandable housing 122, with the expandable filter 130 installed thereon. FIG. 14 is a cross-sectional view, as in FIG. 13, however including an expandable housing inner coating 310, which is not shown in FIG. 13 for clarity. FIG. 15 is a perspective view of the distal end region of the expandable housing 122, with the expandable filter of FIGS. 10-11 installed thereon.

Returning to FIGS. 10 and 11, the shape and size of the holes may differ in different parts of the expandable filter 130. In the distal tubular filter section 514, the holes, exemplified by hole 722, may be longer (in a longitudinal direction) than wide (in a circumferential direction). The holes 722 may be defined in circumferential rows. Holes 722 in adjacent rows may be staggered in the circumferential direction, and partially overlap in the longitudinal and circumferential directions, as shown in FIG. 10. Such staggering and overlapping enables the distal tubular section 514 to easily dilate during assembly, without requiring resilient stretching of the material. This dilation may facilitate insert-ing the impeller 200 into the housing 122 through the distal end of the housing 122. Furthermore, such staggering gen-erally enables disposing the holes 722 closer together and, therefore making the filter 130 more transparent to blood flow.

The distal outer foil 520 (FIG. 13) may be heat sealed, such as by welding, through the holes 722 of the distal tubular filter section 514 extend to a proximal section of the flexible atraumatic tip 120. Each hole 722 in the distal tubular filter section 514 has an enlarged portion located centrally in a longitudinal slot. After the insertion of the impeller 200 and the return of the distal tubular section 514 to its normal diameter, the enlarged portion advantageously has a relatively large open contact area for attachment of the distal outer foil 520 to the flexible atraumatic tip 120.

The expandable filter 130 further includes a transitional zone 724 (FIG. 10) where the distal tubular filter section 514 and the tapered filter section 518 meet. Holes, exemplified by hole 726, in the transitional zone 724 are longer and wider than adjacent holes of the tapered filter section 518. Preferably, the holes 726 in the transitional zone 724 are at least twice as large as the adjacent holes, exemplified by hole 728, in the tapered filter section 518. In one embodiment, for each pair of circumferentially adjacent holes 728 in a row of the tapered filter section 518, the transitional zone 724 has one hole 726 that circumferentially straddles the two holes 728. Thus, the number of holes in a circumferential row in the transitional zone 724 may be half the number of holes in a circumferential row in the tapered filter section 518. In some other embodiments, other ratios may be used, such as 3:1, 4:1 or 3:2. Each hole 726 in the transitional zone 724 may be about twice, thrice or another multiple as long (in the longitudinal direction) and about twice, thrice or another multiple as wide (in the circumferential direction) as the hole 728 in the tapered filter section 518, depending on the ratio of the number of holes 728 in one row of the tapered filter section 518 to the number of holes 726 in one row of the transitional zone 724.

The dimensions and shapes of the holes 702-706 and 728 and dimensions of the struts 714-716 should be chosen such that, when the tapered filter section 518 is fully open, the housing 122 can be inserted into the tapered filter section 518, without exceeding limits of elastic deformation of the material. For example, the length of two circumferentially adjacent struts 714-716 (on zigzag of a zigzag circumfer-ential ring), multiplied by the number of apertures 702-706 in a circumferential row, should about equal the circumfer-ence of a fully expanded housing 122, taking into account any local elastic deformation of the filter material.

Adjacent holes 726 in the transitional zone 724 are separated from each other by struts that are wider than an adjacent strut 714-716 of the tapered filter section 518. These wider struts stabilize the larger holes 726. When the distal outer foil 520 is placed over of the distal tubular filter section 514, longitudinally proximally up to the transitional zone 724, the distal outer foil 520 at least partially covers, and therefore reduces the effective size of, the first one or more rows of the holes 726 in the transitional zone 724. In some cases, these reduced hole sizes may lead to blood damage or increased risk of clotting. Therefore, the holes 726 in the transitional zone 724 should be chosen to be larger than holes in the tapered filter section 518.

As can be seen in FIG. 10, the holes 728 in a distal region of the tapered filter section 518 are narrower, in a circum-ferential direction, than the holes 702-706 in a proximal region of the tapered filter section 518. In other words, sizes of the apertures 702-706 increase monotonically in the proximal direction, along the longitudinal axis. In addition, in the distal tubular filter section 514, the holes 722 take the form of narrow axial slits, which are offset from each other in a circumferential direction. This is advantageous, as narrow holes can widen when the expandable filter 130 is expanded at the distal tubular filter section 514 and the distal region of the tapered filter section 518, such as when the impeller 200 is inserted into the housing 122. Wider holes are bounded by thicker struts, particularly in the tapered filter section 518. The struts have a width of between about 30 μm in the distal region, and about 60 μm in the proximal region, of the tapered filter section 518. Preferably, the largest diameter of the holes in the tapered filter section 518 is between about 300 μm and about 500 μm.

In the embodiment shown in FIG. 10, the proximal tubular filter section 516 has no holes. However, holes in the proximal tubular filter section 516 may be desirable, such as when the proximal outer foil 522 is placed over the proximal tubular filter section 516 (FIG. 8), which in turn may be situated over the intermediate tubular housing part 504. The proximal outer foil 522 fixes the expandable filter 130 to the housing 122, and since the tubular housing part 504 may be coated with PU and the proximal outer foil 522 may also be made of PU, they can easily be heat sealed or welded together through such holes. However, if both the filter 130 and the proximal outer foil 522 are made of compatible materials, such as PU, the filter 130 and the proximal outer foil 522 can be directly joined together, such as by applying heat.

When the expandable filter 130 in FIGS. 10 and 11 is disposed on the expanded housing 122, as shown e.g., in FIG. 13, the distal tubular filter section 514 may be prefer-ably disposed on top of the distal bearing 512 and the flexible atraumatic tip 120. The distal tubular filter section 514 may be covered with the distal outer foil 520 to fasten the expandable filter 130 to the intravascular blood pump 100.

Figure 16:
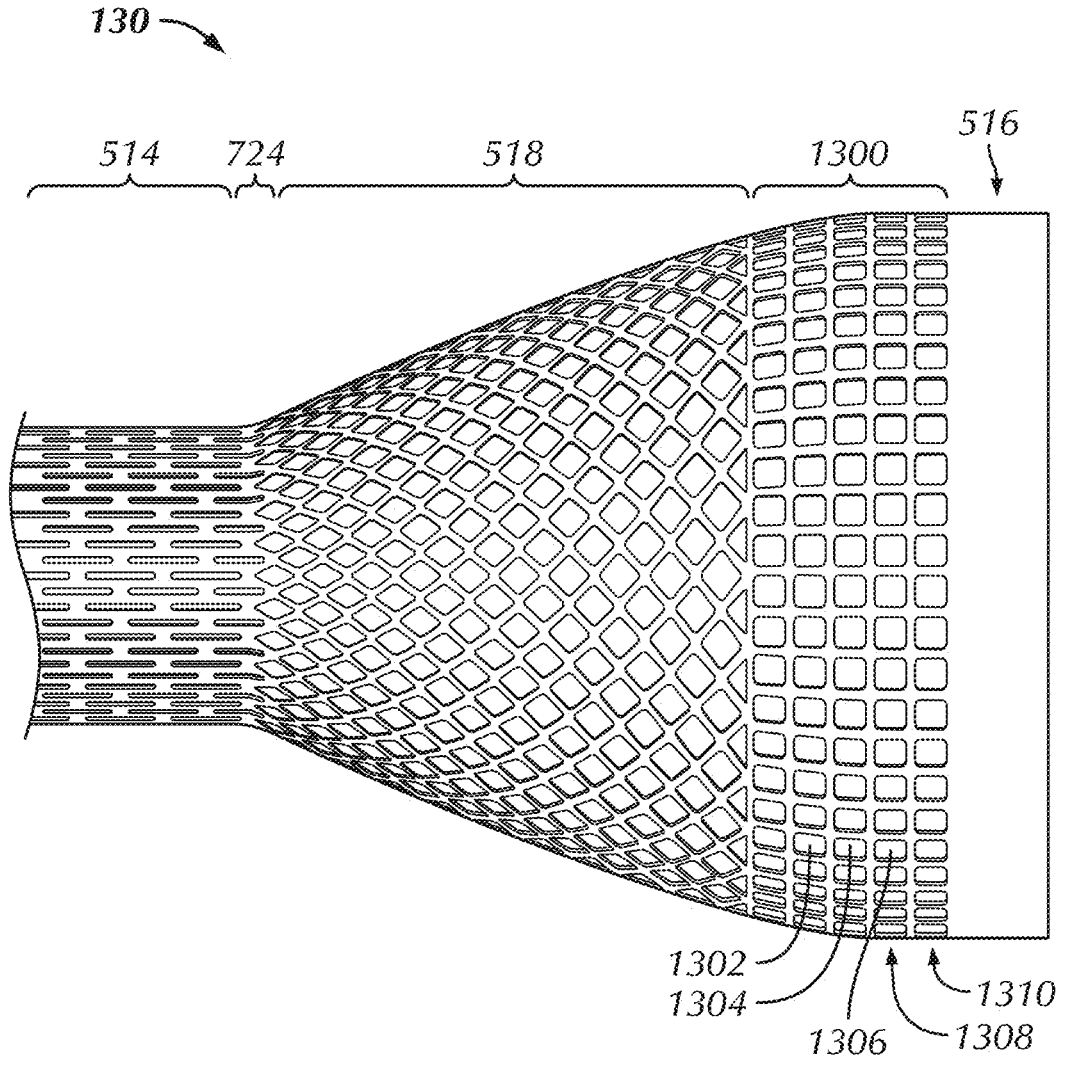
FIG. 16 is a side view of the expandable filter of FIGS. 10-11.

The proximal tubular filter section 516 has a relatively large diameter. If this diameter is not likely to change significantly during assembly of the intravascular blood pump 100, i.e., the proximal opening of the filter 130 is not likely to be significantly stretched, any holes defined in this section will not be significantly deformed during assembly. Thus, these holes can be square or another shape, and the holes can be at least partially defined by circumferential rings of struts. FIG. 16 shows such an embodiment. FIG. 16 is a side view of the expandable filter 130 of FIGS. 10 and 11, according to an alternative embodiment of the present invention.

The expandable filter 130 of FIG. 16 includes a band 1300 of several parallel rings of holes, exemplified by holes 1302, 1304 and 1306 and rings 1308 and 1310. All the rings 1308-1310 have the same number of holes 1302-1306, and the holes 1302-1306 are largely equal sized. Consequently, the ratio of total hole area to total strut area within the band 1300 may be relatively high, compared to other portions of the filter 130. A high hole-to-strut ratio may be advanta-geous, because it makes the filter 130 more transparent to blood flow, which reduces risk of hemolysis and clotting. The ratio of total hole area to total filter 130 area exposed to blood should be at least about 60%, preferably at least about 70% and more preferably at least about 80%. This band 1300 can be combined with the large holes 726 in the transitional zone 724 discussed herein, with respect to FIG. 10.

Descriptions of hole and aperture shape are given for expanded filters 130. When a filter 130 is compressed, such as by folding, the hole shapes may change drastically. Indeed, it is the ability of the struts to bend that makes the filters 130 easy to compress.

Figure 17:
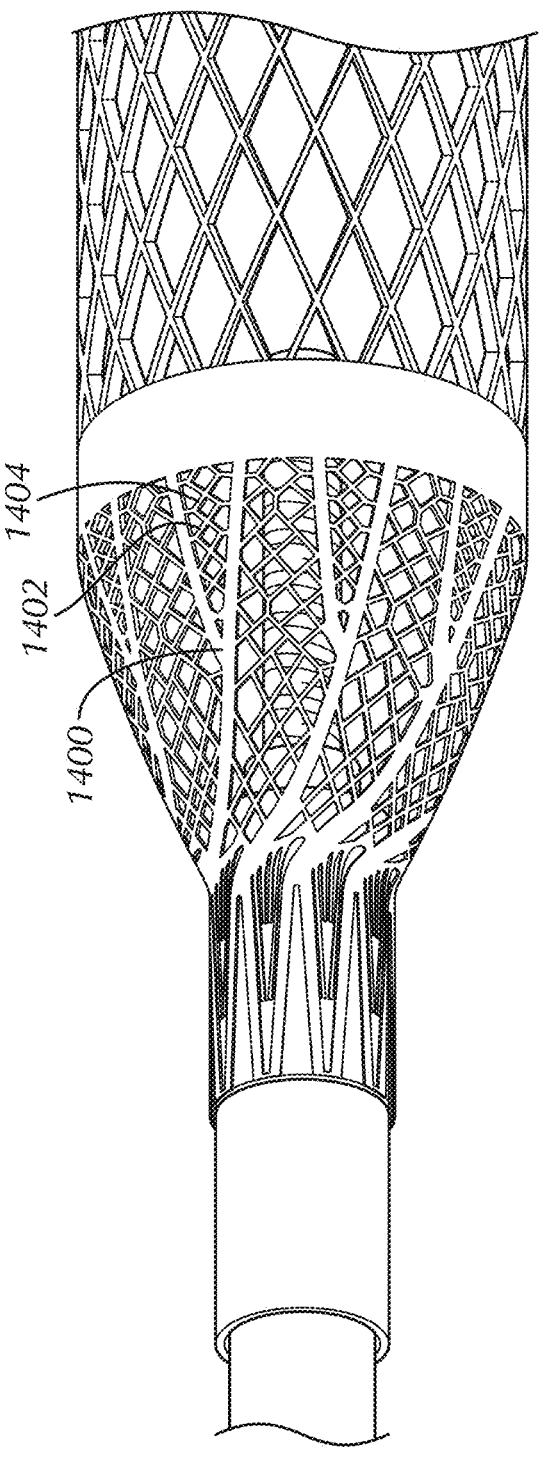
FIG. 17 is a perspective view of the distal end region of the expandable housing of FIGS. 13-14, with an expandable filter similar to that of FIGS. 10-11 and/or 16, but with a different pattern of apertures, installed thereon.

FIG. 17 is a perspective view of the distal end region of the expandable housing of FIGS. 13-14, with an expandable filter similar to that of FIGS. 10-11 and/or 16, but with a different pattern of apertures, installed thereon. For example, some of the struts are forked, as exemplified by strut 1400. Some of the struts, such as forked strut 1400, may be wider than other struts. Some of the struts, exemplified by struts 1402 and 1404, extend between respective pairs of tines of the forks. Thus, a plurality of the first struts and a plurality of the second struts extend between a pair of the tines and collectively define a plurality of the apertures therebetween. Each first strut that comprises a fork may be wider than each first strut that does not comprise a fork.

Optionally, one or more of the struts may register over respective struts of the housing 122. As shown in FIG. 13, the housing 122 includes struts, represented by strut 300, as discussed with respect to FIGS. 6 and 7. Housing struts 300 are referred to herein as third struts. Groups of these third struts, represented by strut 1000 (FIG. 13), collectively define apertures therethrough, represented by aperture 1002 (FIG. 13). At least some of the first and second struts, i.e., struts in the filter (see FIG. 10), such as the forked struts 1400 (FIG. 17), register radially over respective ones of the third struts for support.

Figure 18:
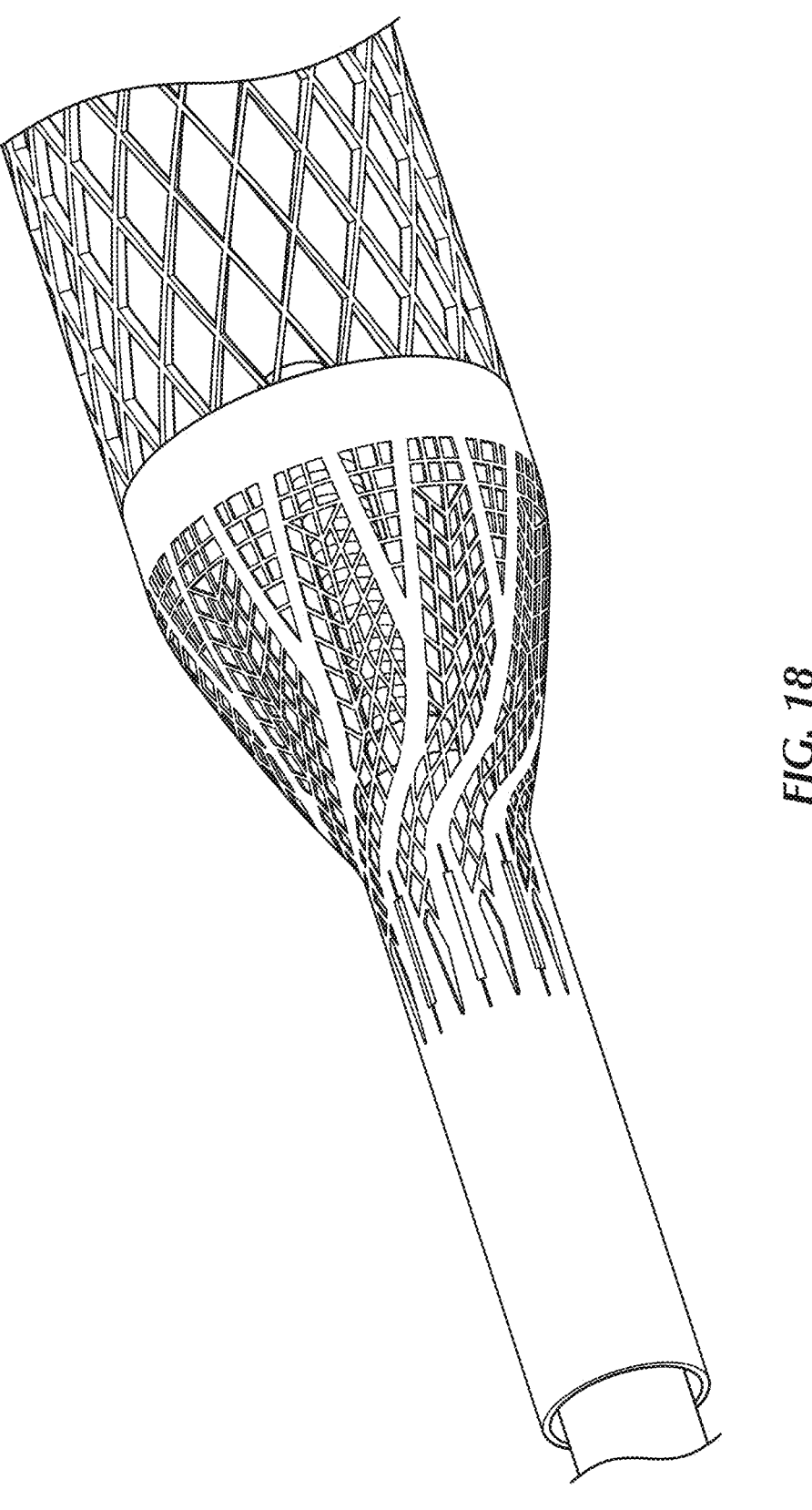
FIG. 18 is a perspective view of the distal end region of the expandable housing of FIGS. 13-14, with an expandable filter similar to that of FIG. 17 installed thereon, but with a further different aperture pattern that is different from the aperture pattern of FIG. 17.

FIG. 18 is a perspective view of the distal end region of the expandable housing of FIGS. 13-14, with an expandable filter similar to that of FIG. 17 installed thereon, but with a different aperture pattern, according to another alternative embodiment of the present invention.

Figure 19:
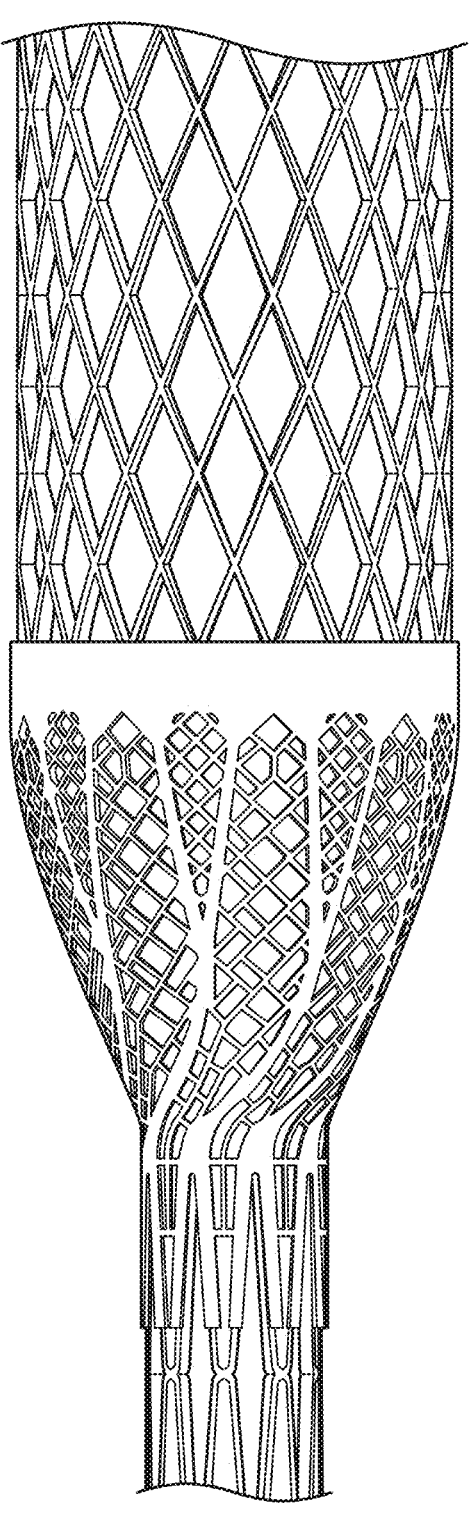
FIG. 19 is a side view of the distal end region of an expandable housing of FIGS. 13-14, with an expandable filter similar to that of FIG. 17 installed thereon.

FIG. 19 is a side view of the distal end region of the expandable housing of FIGS. 13-14, with an expandable filter similar to that of FIG. 17 installed thereon, according to yet another alternative embodiment of the present invention.

Figure 20:
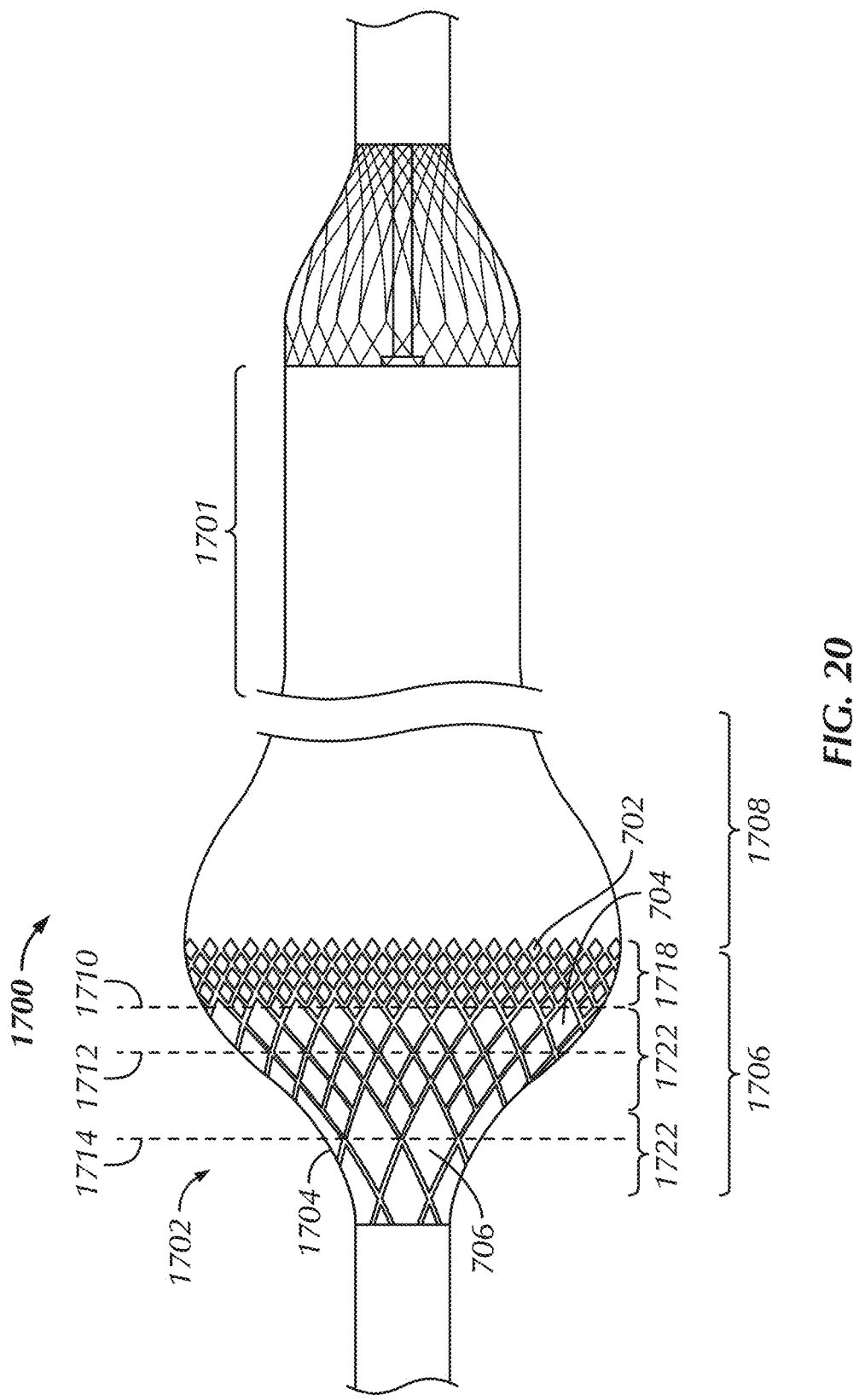
FIG. 20 is a side view of the distal end region of an expandable housing of FIGS. 13-14, with a relatively long inflow cannula and a bulbous expandable filter having an enlarged inflow area installed thereon.
Figure 21:
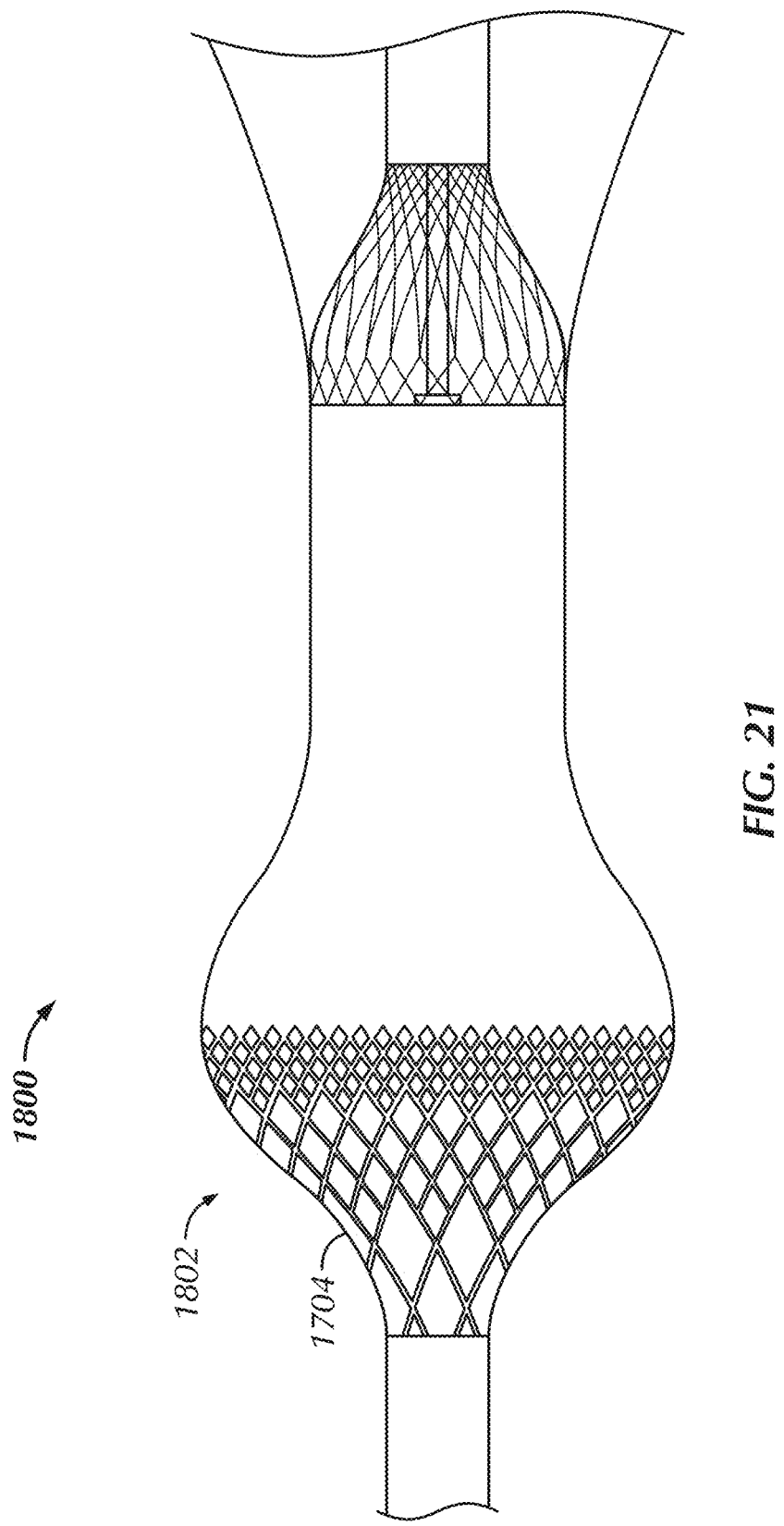
FIG. 21 is a side view of the distal end region of an expandable housing of FIGS. 13-14, with a downstream tubing, rather than a long inflow cannula, and a bulbous expandable filter having an enlarged inflow area installed thereon.

FIG. 20 is a side view of the distal end region of an expandable housing of FIGS. 13-14, with a long inflow cannula 1701 and a bulbous expandable filter 1700 having an enlarged inflow area 1702 installed thereon. FIG. 21 is a side view of the distal end region of an expandable housing of FIGS. 13-14, showing an outflow cannula and without a long inflow cannula, and a bulbous expandable filter 1800 having an enlarged inflow area 1802 installed thereon, but in other respects similar to FIG. 20.

The bulbous expandable filters 1700 and 1800 provide enlarged inflow areas 1702 and 1802 to the intravascular blood pump 100, which improves the flow characteristic of the pump. The enlarged inflow areas 1702 and 1802 are covered with a filter 1704 similar to FIGS. 13-15, but with yet larger apertures.

The filter 130 includes a distal portion 1706 and a proximal portion 1708. The distal portion 1706 monotonically increases in diameter in a proximal direction along the longitudinal axis. The proximal portion 1708 monotonically decreases in diameter in the proximal direction along the longitudinal axis.

At least a portion of the plurality of apertures 702-706 may be disposed on the distal portion 1706. In some embodiments, the proximal portion 1708 may be devoid of apertures.

In general, sizes of the apertures of the plurality of apertures 702-706 increase along the longitudinal axis, in the distal direction, although the increase need not necessarily be monotonic. The apertures 702-706 are arranged in a plurality of generally circumferential, relative to the longitudinal axis, rows of equal-sized apertures, exemplified by rows 1710, 1712 and 1714. Ones of the rows 1710-1714 have different numbers of the apertures 702-706 from others of the rows 1710-1714. For example, a first row 1710 (indicated by a dashed line) of the plurality of generally circumferential rows comprises more apertures 702 than a second row 1712 of the plurality of generally circumferential rows. Each aperture 702 of the first row 1710 has a smaller area than each aperture 704 of the second row 1712.

The apertures 702-706 may be arranged in a plurality of generally circumferential, relative to the longitudinal axis, bands of about equal-sized apertures, exemplified by bands 1716, 1718 and 1720. Size of the apertures 702-706 in each of the plurality of bands 1718-1722 increases monotonically along the longitudinal axis. That is, in general, the apertures in band 1720 are larger than the apertures in band 1718. However, apertures in a given row may be larger or smaller than apertures in another row of the same band, because although the two rows have the same number of apertures, the two rows may have different circumferences. In the embodiment shown in FIG. 20, the size of the apertures 702-706 in each of the plurality of bands 1718-1722 increases monotonically along the longitudinal axis in the distal direction. Other aspects of the aperture sizes and arrangements are similar to those discussed with respect to FIG. 10.

As noted, the distal end region of the expandable housing shown in FIG. 21 is similar to that shown in FIG. 20, except that the expandable housing in FIG. 21 includes a flexible outflow cannula and does not include a relatively long inflow cannula. For example, in some embodiments, the distance between the blood inlet and the impeller may be less than half the length of the outflow cannula. In some embodiments, the distance between the blood inlet and the impeller may be less than 10% of the length of the outflow cannula.

Figure 22:
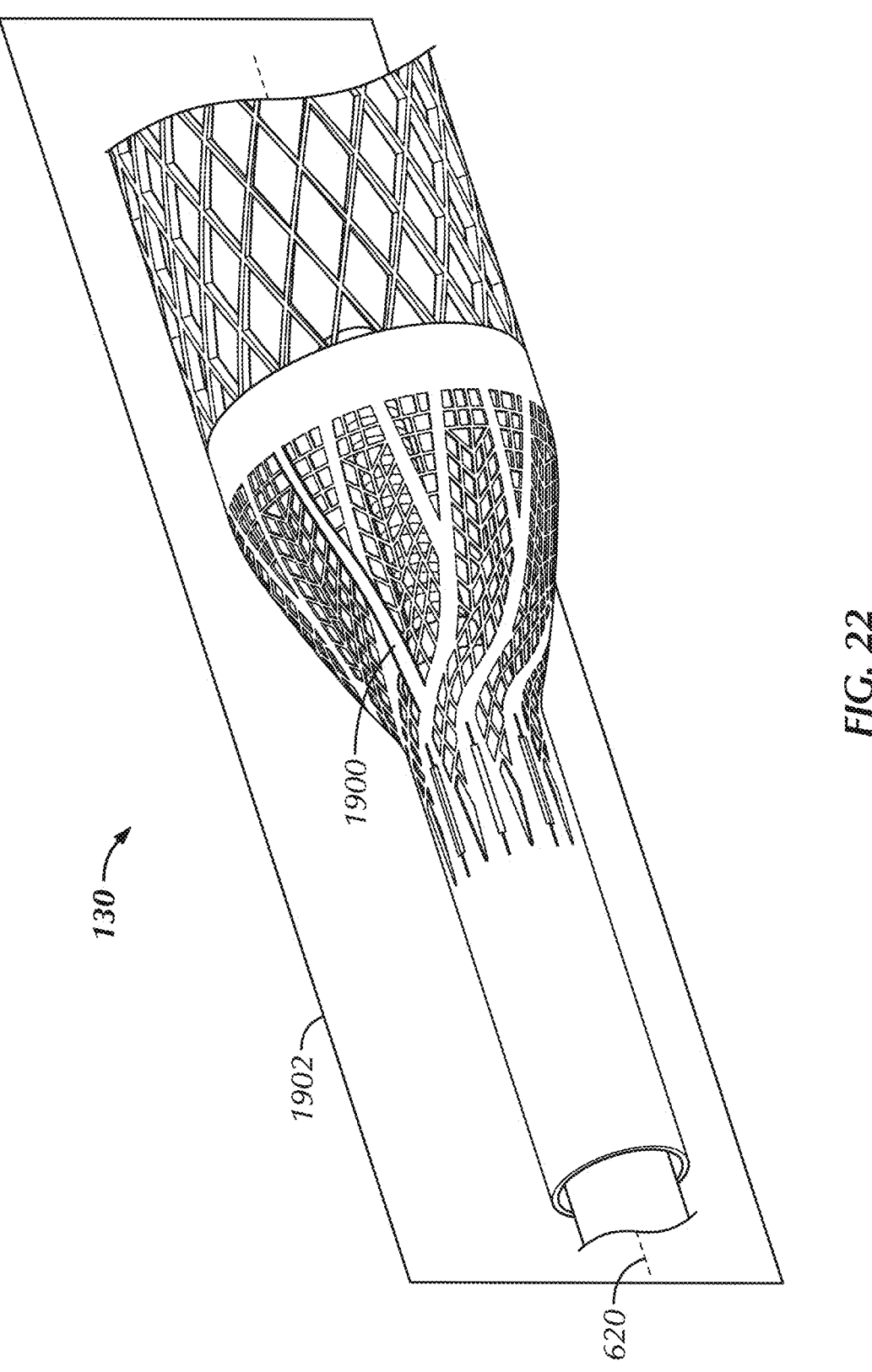
FIG. 22 shows a perspective view of an expandable filter formed of a mesh of filaments and mounted on a distal end region of the expandable housing (FIGS. 6-8) of the intravascular blood pump of FIGS. 1 and 5, similar to that of FIG. 9, but with some longitudinal struts.

FIG. 22 is a perspective view of the distal end region of the expandable housing of FIGS. 13-14, with an expandable filter similar to that of FIG. 17, but with some longitudinal struts, exemplified by longitudinal strut 1900. Each longitudinal strut 1900 lies in a respective plane, exemplified by plane 1902, that contains the longitudinal axis 620. As used herein, the phrase a "plane that contains" a line means the line lies completely in the plane. Although FIG. 22 shows only one longitudinal strut 1900, the filter 130 may include additional longitudinal struts (not shown).

In some embodiments, the blood pumps may have resiliently radially-compressible ("crimpable") pump housings, and in some cases radially-compressible impellers, to facilitate inserting the pumps into patients. A compressible-housing blood pump may be inserted into a patient while the blood pump and impeller are in compressed states, and then after the blood pump is properly positioned, the pump housing and the impeller may be allowed to radially expand.

Figure 23:
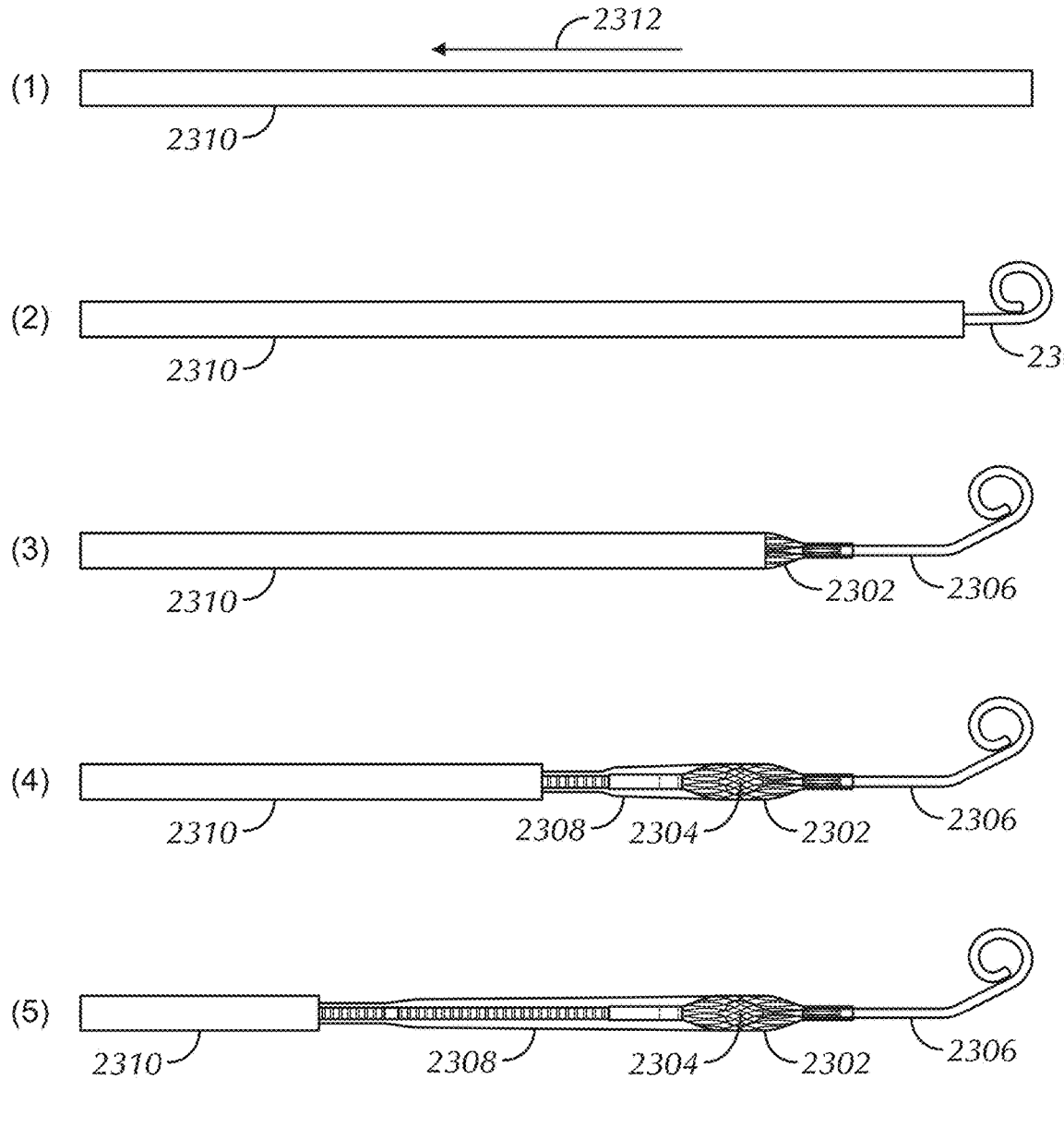
FIG. 23 is a graphical illustration of stages for expanding a blood pump, according to one embodiment.

FIG. 23 is a graphical illustration of an example of such a process. FIG. 23 provides a side view of the blood pump 2300 in six stages ((1) to (6)) of emerging from a tubular sheath 2310, as the tubular sheath 2310 is withdrawn, relative to the blood pump 2300, as indicated by an arrow 2312. As the tubular sheath 2310 may be withdrawn, portions of the blood pump 2300, particularly the mesh structure 2302 and the impeller 2304, resiliently radially expand, and the pig tail 2306 coils.

Figures 24, 25:
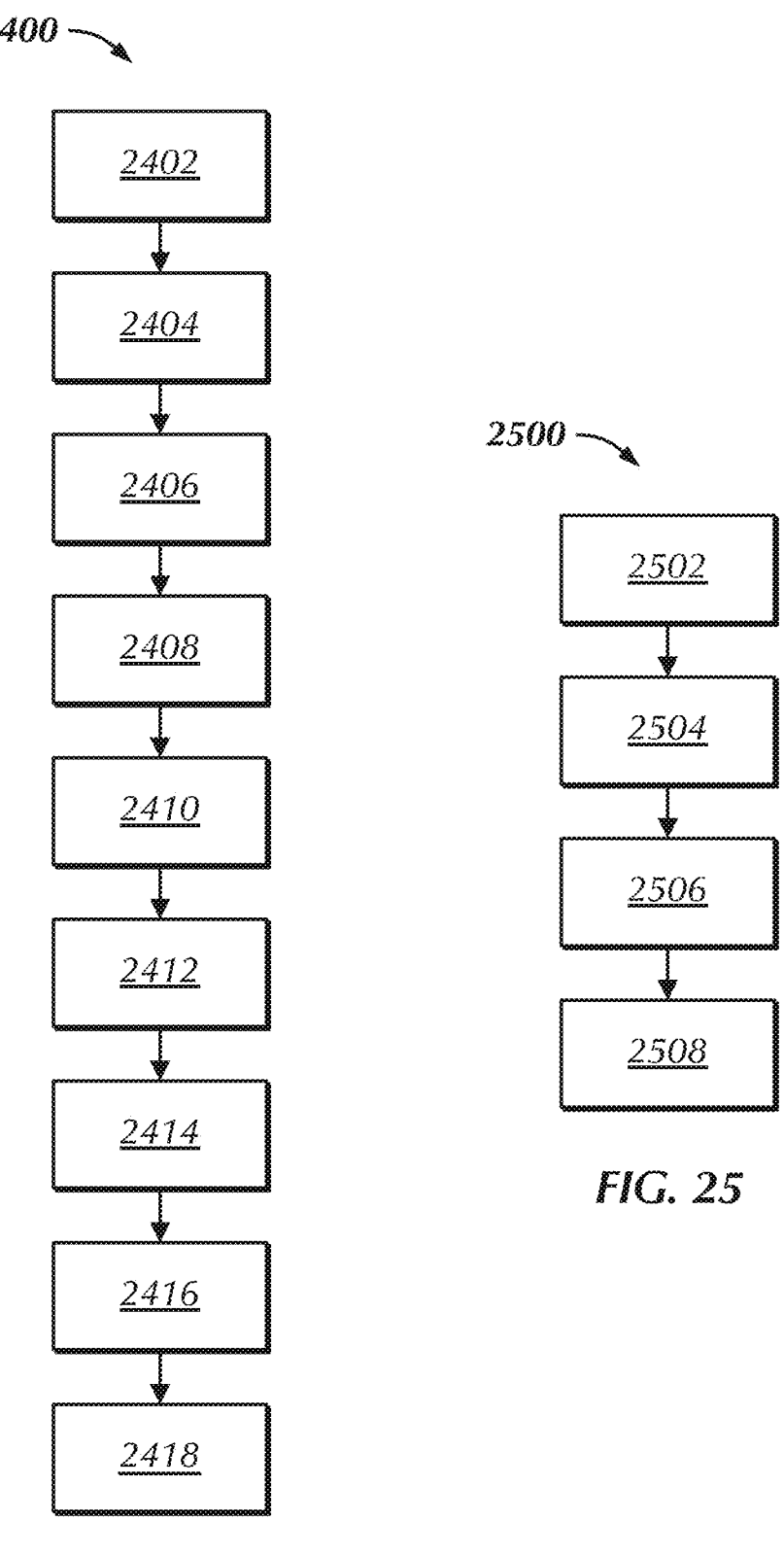
FIGS. 24-25 are flowcharts of embodiments of methods for crimping a blood pump.

FIG. 24 is a flowchart that schematically illustrates a method 2400 for crimping a blood pump. The method 2400 may, for example, be practiced using a crimp tool, as known in the art. The method includes disposing 2402 the blood pump inside a distal end of a tapered longitudinal tube bore. The tube bore may be defined by an elongated tube. The tube bore may be at least about 30 mm long. The tube bore may have an inside dimension that tapers along the length of the tube bore from (a) at least about a maximum outside dimension of the pump at the distal end of the tube bore to (b) at most about 4 mm in diameter at a proximal end of the tube bore.

At 2404, the blood pump may be translated through the tube bore in a direction toward the proximal end of the tube bore, including contacting an outside surface of the blood pump with an inside surface of the elongated tube as the blood pump translates through the tube bore, thereby crimping the blood pump to produce a crimped blood pump.

In some embodiments, translating the blood pump may include pulling the blood pump through the tube bore. However, in principle, translating the blood pump can involve pushing the blood pump through the tube bore.

In some embodiments, the inside dimension of the distal end of the tube bore may be at least about 7 mm. In some embodiments, the inside dimension of the proximal end of the tube bore may be at most about 4 mm. In some embodiments, the inside dimension of the distal end of the tube bore may be at least about 7 mm, and the inside dimension of the proximal end of the tube bore may be at most about 4 mm. In some embodiments, the tube bore may be at least about 50 mm long. In some embodiments, the tube bore may be at least about 100 mm long. In some embodiments, the tube bore may be at least about 170 mm long. In some embodiments, the tube bore may be at least about 300 mm long.

Optionally, an inside wall of the tube that defines the tapered tube bore may extend at an angle, relative to a longitudinal axis of the tube, of less than about 2°. Optionally, a taper ratio of the tapered tube bore, calculated as a ratio of (a) a change in inside diameter of the tube bore to (b) length of the taper along a longitudinal axis of the tube may be no greater than about 1:14.

Optionally, at 2406, a tubular sheath may be disposed substantially coaxially with the proximal end of the tube bore.

Optionally, at 2408, the crimped blood pump may be translated from the proximal end of the tube bore to the tubular sheath, without substantially altering an outside dimension of the crimped blood pump. Translating 2408 the crimped blood pump from the proximal end of the tube bore to the tubular sheath may include: (a) releasably restraining 2410 a distal end portion of the tubular sheath in a hub. The hub is attached to the proximal end of the tube. The hub defines a hub bore therethrough coaxial with the tube bore. One end of the hub bore is coupled to the proximal end of the tube bore. The other end of the hub bore is configured to receive the distal end portion of the tubular sheath substantially coaxially with the tube bore. Translating 2408 the crimped blood pump from the proximal end of the tube bore to the tubular sheath may also include: (b) translating 2412 the crimped blood pump through the hub bore. Optionally, the method further includes releasing 2414 the distal end portion of the tubular sheath from the hub.

Optionally, the method includes translating 2416 the crimped blood pump out of the tubular sheath and into a vasculature of a patient and allowing 2418 the crimped blood pump to resiliently expand within the vasculature.

FIG. 25 is a flowchart that schematically illustrates another method 2500 for crimping a blood pump. The method 2500 may, for example, be practiced using a frangible crimp tool, as known in the art. The method 2500 includes disposing 2502 the blood pump inside a distal end of a tapered longitudinal tube bore. The tube bore may be defined by an elongated tube. A proximal end of the tube may be coaxially and frangibly attached to a distal end of a tubular sheath. The tubular sheath may have an inside dimension (e.g., an inner diameter). The tube bore may be at least about 30 mm long. The tube bore may have an inside dimension that tapers along the length of the tube bore from (a) at least about a maximum outside dimension of the blood pump at the distal end of the tube bore to (b) about the inside dimension of the tubular sheath at the proximal end of the tube bore.

At 2504, the blood pump may be translated through the tube bore in a direction toward the proximal end of the tube bore, including contacting an outside surface of the blood pump with an inside surface of the elongated tube as the blood pump translates through the tube bore, thereby crimping the blood pump to produce a crimped blood pump. At 2506, the crimped blood pump may be translated from the proximal end of the tube bore to the tubular sheath, without substantially altering an outside dimension of the crimped blood pump. At 2508, the tubular sheath may be frangibly detached from the tube, with the crimped blood pump disposed within the tubular sheath.

While the invention is described through the above-described exemplary embodiments, modifications to, and variations of, the illustrated embodiments may be made without departing from the inventive concepts disclosed herein. For example, although specific parameter values, such as dimensions and materials, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," are used to distinguish respective struts, rings of apertures and/or bands of apertures from one another and are not intended to indicate any particular order or total number of struts, rings of apertures and/or bands of apertures in any particular embodiment. Thus, for example, a given embodiment may include only a second struts, rings of apertures and/or bands of apertures and a third struts, rings of apertures and/or bands of apertures.

What is claimed is:

1. A blood pump, comprising:
   a pump housing having a blood flow inlet;
   a catheter operably coupled to a proximal end of the pump housing, the catheter having an outer diameter that is smaller than an outer diameter of the pump housing;
   a flexible outflow cannula having a proximal end portion operably coupled to the catheter, a plurality of blood flow outlets, and a distal end portion operably coupled to the pump housing, where the pump housing and flexible outflow cannula define a blood flow path from the blood flow inlet of the pump housing to the plurality of blood flow outlets;

an impeller arranged within the pump housing and configured to be rotatable about an axis of rotation for conveying blood from the blood flow inlet to the plurality of blood flow outlets;

wherein the proximal end portion of the flexible outflow cannula has a coupled portion coupled to the catheter and an uncoupled portion extending distally from the coupled portion;

wherein at least one slit is formed through all of the coupled portion and extends to a proximal end of the flexible outflow cannula;

wherein the plurality of blood flow outlets comprise one or more cut outlets; and wherein each slit connects to a proximal end of one of the one or more cut outlets, the cut outlet connected to each slit having a tapered proximal end and extending distally from the uncoupled portion.

2. The blood pump according to claim 1, wherein the at least one slit extends distally from the coupled portion through at least a portion of the uncoupled portion before connecting to a cut outlet.

3. The blood pump according to claim 1, wherein the plurality of blood flow outlets consists of four blood flow outlets, and wherein the four blood flow outlets have exactly one cut outlet or exactly two cut outlets.

4. The blood pump according to claim 3, wherein the flexible outflow cannula comprises an intermediate portion extending between the distal end portion and the proximal end portion, the intermediate portion having an outer diameter that is larger than the outer diameter of the pump housing.

5. The blood pump according to claim 4, wherein each of the plurality of blood flow outlets is positioned at least partially in the intermediate portion, and only the one or more cut outlets are positioned at least partially in both the proximal end portion and the intermediate portion.

6. The blood pump according to claim 1, wherein the cut outlets each comprise a distal portion, a proximal portion, and an intermediate portion between the distal portion and proximal portion, the intermediate portion having substantially parallel sides.

7. The blood pump according to claim 1, further comprising a filter in fluid communication between: (a) an interior volume of a blood vessel in which the blood pump is inserted, external to the pump housing, and (b) the blood flow inlet, the filter comprising a plurality of generally helical first struts wound about a longitudinal axis and a plurality of second struts, the first and second struts collectively defining a plurality of apertures therebetween.

8. The blood pump according to claim 7, wherein the pump housing, the impeller and the filter are each alternatingly radially compressible and radially expandable.

9. The blood pump according to claim 8, wherein the pump housing is configured, when radially compressed, to longitudinally lengthen an amount that depends on an amount by which the pump housing is radially compressed, and the filter is configured, when radially compressed, to longitudinally lengthen an amount that depends on an amount by which the filter is radially compressed such that, for a given amount of radial compression, the filter and the pump housing longitudinally lengthen about equal amounts.

10. The blood pump according to claim 8, wherein the filter comprises a tube having a wall, wherein the plurality of apertures comprises a plurality of openings defined through the wall.

11. The blood pump according to claim 10, wherein the tube comprises a generally funnel-shaped tube.

12. The blood pump according to claim 10, wherein the pump housing comprises a plurality of third struts that collectively define a plurality of third apertures therebetween, and at least some of the first and second struts register radially over respective ones of the plurality of third struts.

13. The blood pump according to claim 10, wherein each strut of at least a subset of the plurality of generally helical first struts comprises a fork that includes a plurality of tines, and wherein two or more of the plurality of generally helical first struts and two or more of the plurality of second struts extend between a pair of the tines and collectively define a plurality of the apertures therebetween.

14. The blood pump according to claim 13, wherein each first strut that comprises a fork is wider than each first strut that does not comprise a fork.

15. The blood pump according to claim 10, wherein the plurality of apertures is arranged in a plurality of generally circumferential, relative to the longitudinal axis, rows of equal-sized apertures, wherein ones of the rows have different numbers of apertures from others of the rows.

16. The blood pump according to claim 15, wherein a first row of the plurality of generally circumferential rows comprises more apertures than a second row of the plurality of generally circumferential rows, and each aperture of the first row has a smaller area than each aperture of the second row.

17. The blood pump according to claim 10, wherein the plurality of apertures are arranged in a plurality of generally circumferential, relative to the longitudinal axis, bands of about equal-sized apertures, wherein size of apertures in each of the plurality of generally circumferential bands increases monotonically along the longitudinal axis.

18. The blood pump according to claim 17, wherein the filter comprises a distal portion and a proximal portion, the distal portion monotonically increases in diameter in a proximal direction along the longitudinal axis, the proximal portion monotonically decreases in diameter in the proximal direction along the longitudinal axis and at least a portion of the plurality of apertures is disposed on the distal portion.

19. A blood pump, comprising:

a pump housing having a blood flow inlet;

a catheter operably coupled to a proximal end of the pump housing, the catheter having an outer diameter that is smaller than an outer diameter of the pump housing;

a flexible outflow cannula having a proximal end portion operably coupled to the catheter, a plurality of blood flow outlets, and a distal end portion operably coupled to the pump housing, where the pump housing and flexible outflow cannula define a blood flow path from the blood flow inlet of the pump housing to the plurality of blood flow outlets;

an impeller arranged within the pump housing and configured to be rotatable about an axis of rotation for conveying blood from the blood flow inlet to the plurality of blood flow outlets;

wherein the proximal end portion of the flexible outflow cannula has a coupled portion coupled to the catheter and an uncoupled portion extending distally from the coupled portion;

wherein at least one slit is formed through all of the coupled portion and extends to a proximal end of the flexible outflow cannula;

wherein the plurality of blood flow outlets comprise one or more cut outlets;

wherein each slit connects to a proximal end of one of the one or more cut outlets, the cut outlet connected to each slit having a tapered proximal end and extending distally from the uncoupled portion; and wherein either (i) the at least one slit is configured to allow at least a first portion of the coupled portion of the proximal end portion to overlap a second portion of the coupled portion of the proximal end portion, or (ii) the at least one slit is configured to prevent a first portion of the coupled portion of the proximal end portion from overlapping with a second portion of the coupled portion of the proximal end portion.

\* \* \* \* \*